US012733816B2

(12) United States Patent
Chun et al.

(10) Patent No.: US 12,733,816 B2
(45) Date of Patent: Sep. 15, 2026

(54) ACOUSTO-MECHANIC SENSORS AND APPLICATIONS OF SAME

(71) Applicants: NORTHWESTERN UNIVERSITY, Evanston, IL (US); BOARD OF REGENTS, THE UNIVERSITY OF TEXAS SYSTEM, Austin, TX (US)

(72) Inventors: Keum San Chun, Evanston, IL (US); Jong Yoon Lee, Evanston, IL (US); Youn Joung Kang, Evanston, IL (US); Hyoyoung Jeong, Evanston, IL (US); John A. Rogers, Wilmette, IL (US); Shuai Xu, Evanston, IL (US)

(73) Assignees: NORTHWESTERN UNIVERSITY, Evanston, IL (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 181 days.

(21) Appl. No.: 18/285,271

(22) PCT Filed: Apr. 5, 2022

(86) PCT No.: PCT/US2022/023397
§ 371 (c)(1),
(2) Date: Oct. 2, 2023

(87) PCT Pub. No.: WO2022/216650
PCT Pub. Date: Oct. 13, 2022

(65) Prior Publication Data

US 2024/0358259 A1 Oct. 31, 2024

Related U.S. Application Data

(60) Provisional application No. 63/171,483, filed on Apr. 6, 2021.

(51) Int. Cl.
*A61B 5/00* (2006.01)
*A61B 5/11* (2006.01)

(52) U.S. Cl.
CPC .......... *A61B 5/0093* (2013.01); *A61B 5/1126* (2013.01); *A61B 5/6824* (2013.01);
(Continued)

(58) Field of Classification Search
CPC .... A61B 2560/0209; A61B 2560/0214; A61B 2560/045; A61B 2560/0462;
(Continued)

(56) References Cited

U.S. PATENT DOCUMENTS

2014/0046222 A1 2/2014 Yaksh et al.
2017/0164876 A1* 6/2017 Hyde .................... A61B 5/1118

FOREIGN PATENT DOCUMENTS

KR 101638680 B1 7/2016
KR 101759621 B1 7/2017
(Continued)

OTHER PUBLICATIONS

G. Yosipovitch, M. W. Greaves and M. Schmelz, Itch. Lancet. 361, 690-694 (2003).
(Continued)

*Primary Examiner* — George Manuel
(74) *Attorney, Agent, or Firm* — troutman pepper locke; Tim Tingkang Xia, Esq.

(57) ABSTRACT

This invention in one aspect relates to an acousto-mechanic sensor includes at least one inertial measurement unit (IMU) for operably detecting vibratory and motion signatures of physiological processes; and a plurality of electronic components comprising a microcontroller unit coupled to the at least one IMU for receiving data from the at least one IMU and processing the received data, and a wireless communication system for wireless data transmission. The novel
(Continued)

acousto-mechanic sensor has broad applications ranging from the assessing the efficacy of drugs for conditions that cause itch to monitoring disease severity and treatment response.

41 Claims, 22 Drawing Sheets

(52) U.S. Cl.
CPC .......... *A61B 5/6826* (2013.01); *A61B 5/6832* (2013.01); *A61B 5/725* (2013.01); *A61B 5/7257* (2013.01); *A61B 5/7267* (2013.01); *A61B 5/7405* (2013.01); *A61B 5/742* (2013.01); *A61B 5/7455* (2013.01); *A61B 2560/0209* (2013.01); *A61B 2560/0214* (2013.01); *A61B 2560/045* (2013.01); *A61B 2560/0462* (2013.01); *A61B 2562/0219* (2013.01); *A61B 2562/14* (2013.01); *A61B 2562/164* (2013.01); *A61B 2562/166* (2013.01); *A61B 2562/225* (2013.01)

(58) Field of Classification Search
CPC ........ A61B 2562/0219; A61B 2562/14; A61B 2562/164; A61B 2562/166; A61B 2562/225; A61B 5/0057; A61B 5/0093; A61B 5/1126; A61B 5/6824; A61B 5/6825; A61B 5/6826; A61B 5/6832; A61B 5/725; A61B 5/7257; A61B 5/7267; A61B 5/7405; A61B 5/742; A61B 5/7455; A61B 5/00; A61B 5/11; G16H 40/63; G16H 50/20; G16H 50/70
See application file for complete search history.

(56) References Cited

FOREIGN PATENT DOCUMENTS

| | | | |
|---|---|---|---|
| KR | 20200058737 | A | 5/2020 |
| WO | 2019161277 | A1 | 8/2019 |

OTHER PUBLICATIONS

A. Bathe, E. Weisshaar, U. Matterne, Chronic pruritus-more than a symptom: a qualitative investigation into patients' subjective illness perceptions. J. Adv. Nurs. 69, 316-326 (2013).
M. Shive, E. Linos, T. Berger, M. Wehner, M.-M. Chren, Itch as a patient-reported symptom in ambulatory care visits in the United States. J. Am. Acad. Dermatol. 69, 550-556 (2013).
T. E. Shaw, G. P. Currie, C. W. Koudelka, E. L. Simpson, Eczema prevalence in the United States: data from the 2003 National Survey of Children's Health. J. Invest. Dermatol. 131, 67-73 (2011).
S. L. Chamlin, C. L. Mattson, I. J. Frieden, M. L. Williams, A. J. Mancini, D. Cella, M.-M. Chren, The price of pruritus: sleep disturbance and cosleeping in atopic dermatitis. Arch. Pediatr. Adolesc. Med. 159, 745-750 (2005).
K. Hon, T. Leung, K. Wong, C. Chow, A. Chuh, P. Ng, Does age or gender influence quality of life in children with atopic dermatitis? Clin. Exp. Dermatol. 33, 705-709 (2008).
D. Camfferman, J. D. Kennedy, M. Gold, A. J. Martin, K. Lushington, Eczema and sleep and its relationship to daytime functioning in children. Sleep Med. Rev. 14, 359-369 (2010).
R. Sack, J. Hanifin, Scratching below the surface of sleep and itch. Sleep Med. Rev. 14, 349-350 (2010).
A. B. Fishbein, O. Vitaterna, I. M. Haugh, A. A. Bavishi, P. C. Zee, F. W. Turek, S. H. Sheldon, J. I. Silverberg, A. S. Paller, Nocturnal eczema: review of sleep and circadian rhythms in children with atopic dermatitis and future research directions. J. Allergy Clin. Immunol. 136, 1170-1177 (2015).
A. B. Fishbein, K. Mueller, L. Kruse, P. Boor, S. Sheldon, P. Zee, A. S. Paller, Sleep disturbance in children with moderate/severe atopic dermatitis: a case-control study. J. Am. Acad. Dermatol. 78, 336-341 (2018).
J. I. Silverberg, N. K. Garg, A. S. Paller, A. B. Fishbein, P. C. Zee, Sleep disturbances in adults with eczema are associated with impaired overall health: a US population-based study. J. Invest. Dermatol. 135, 56-66 (2015).
M. K. LeBourgeois, D. C. Dean, S. C. Deoni, M. Kohler, S. Kurth, A simple sleep EEG marker in childhood predicts brain myelin 3.5 years later. NeuroImage. 199, 342-350 (2019).
G. Kiebert, S. V. Sorensen, D. Revicki, S. C. Fagan, J. J. Doyle, J. Cohen, D. Fivenson, Atopic dermatitis is associated with a decrement in health-related quality of life. Int. J. Dermatol. 41, 151-158 (2002).
C. S. Murray, J. L. Rees, Are subjective accounts of itch to be relied on? The lack of relation between visual analogue itch scores and actigraphic measures of scratch. Acta Derm. Vener. 91, 18-23 (2011).
A. Moreau, P. Anderer, M. Ross, A. Cerny, T. H. Almazan, B. Peterson, Detection of nocturnal scratching movements in patients with atopic dermatitis using accelerometers and recurrent neural networks. IEEE J. Biomed. Health Inform. 22, 1011-1018 (2017).
K. Lee, X. Ni, J. Y. Lee, H. Arafa, J. P. David, S. Xu, R. Avila, M. Irie, J. H. Lee, R. L. Easterlin, Mechano-acoustic sensing of physiological processes and body motions via a soft wireless device placed at the suprasternal notch. Nat. Biomed. Eng. 4, 148-158 (2020).
Y. Shao, V. Hayward, Y. Visell, Spatial patterns of cutaneous vibration during whole-hand haptic interactions. PNAS, 113, 4188-4193 (2016).
A. Ikoma, T. Ebata, L. Chantalat, K. Takemura, F. Mizzi, M. Poncet, D. Leclercq, Measurement of nocturnal scratching in patients with pruritus using a smartwatch: initial clinical studies with the itch tracker app. Acta Derm. Vener. 99, 268-273 (2019).
J. Lee, D. Cho, J. Kim, E. Im, J. Bak, K. H. Lee, K. H. Lee, J. Kim, Itchtector: a wearable-based mobile system for managing itching conditions. Proc. CHI Conf. Hum. Factor. Comput. Syst. 893-905 (2017).
K. Benjamin, K. Waterston, M. Russell, O. Schofield, B. Diffey, J. L. Rees, The development of an objective method for measuring scratch in children with atopic dermatitis suitable for clinical use. J. Am. Acad. Dermatol. 50, 33-40 (2004).
M. Wiertlewski, J. Lozada, V. Hayward, The spatial spectrum of tangential skin displacement can encode tactual texture. IEEE Trans. Robot. 27, 461-472 (2011).
M. Wiertlewski, V. Hayward, Mechanical behavior of the fingertip in the range of frequencies and displacements relevant to touch. J. Biomech. 45, 1869-1874 (2012).
B. Delhaye, V. Hayward, P. Lefèvre, J.-L. Thonnard, Texture-induced vibrations in the forearm during tactile exploration. Front. Behav. Neurosci. 6, 37 (2012).
S. Saeb, L. Lonini, A. Jayaraman, D. C. Mohr , K. P. Kording, The need to approximate the use-case in clinical machine learning. Gigascience. 6, gix019 (2017).
T. Ebata, H. Aizawa, R. Kamide, An infrared video camera system to observe nocturnal scratching in atopic dermatitis patients. J. Dermatol. 23, 153-155 (1996).
T. Ebata, S. Iwasaki, R. Kamide, M. Niimura, Use of a wrist activity monitor for the measurement of nocturnal scratching in patients with atopic dermatitis. Br. J. Dermatol. 144, 305-309 (2001).
Y. Noro, Y. Omoto, K. Umeda, F. Tanaka, Y. Shiratsuka, T. Yamada, K. Isoda, K. Matsubara, K. Yamanaka, E. C. Gabazza, Novel acoustic evaluation system for scratching behavior in itching dermatitis: rapid and accurate analysis for nocturnal scratching of atopic dermatitis patients. J. Dermatol. 41, 233-238 (2014).
O. Crasborn, H. Sloetjes, E. Auer, P. Wittenburg, Combining video and numeric data in the analysis of sign languages with the ELAN annotation software. 2nd workshop on the representation and processing of sign languages: lexicographic matters and didactic scenarios. 82-87 (2006).
S. Arlot, A. Celisse, A survey of cross-validation procedures for model selection. Statistics surveys. 4, 40-79 (2010).

(56) References Cited

OTHER PUBLICATIONS

R. Kohavi, A study of cross-validation and bootstrap for accuracy estimation and model selection. IJCAI. 14, 1137-1145 (1995).
J. L. Fleiss, J. Cohen, B. S. Everitt, Large sample standard errors of kappa and weighted kappa. Psychol. Bull. 72, 323 (1969).
J. R. Landis and G. G. Koch, The measurement of observer agreement for categorical data. Biometrics. 159-174 (1977).
Korean Intellectual Property Office (ISR/KR), “International Search Report for PCT/US2022/023397”, Korea, Jul. 25, 2022.
Mary Patricia Smith et al. Emerging Methods to Objectively Assess Pruritus in Atopic Dermatitis. Published in: Dermatol Ther (Heidelb), Jun. 29, 2019, vol. 9, pp. 407-420.
Keum San Chun et al. A skin-conformable wireless sensor to objectively quantify symptoms of pruritus. Published in: Science Advances, Apr. 30, 2021, vol. 7, No. 18, pp. 1-11.
EPO “Supplementary European Search Report for EP Application No. 22785259.7”, Hague, Germany, Jun. 19, 2024.

* cited by examiner

| Summary | Algorithm Validation Study |
| --- | --- |
| Number of subjects | 10 |
| Age | 22 – 27 (24 ± 1.6) |
| Gender Ratio (M:F) | 1 : 1 |
| Avg. Trial Duration | 36.2 s |
| Total Duration | 3 h 16 m |
| Total Non-Scratching Time | 28 m |
| Scratching Time | 2 h 48 m |
| Condition | Healthy Normal |

FIG. 5A

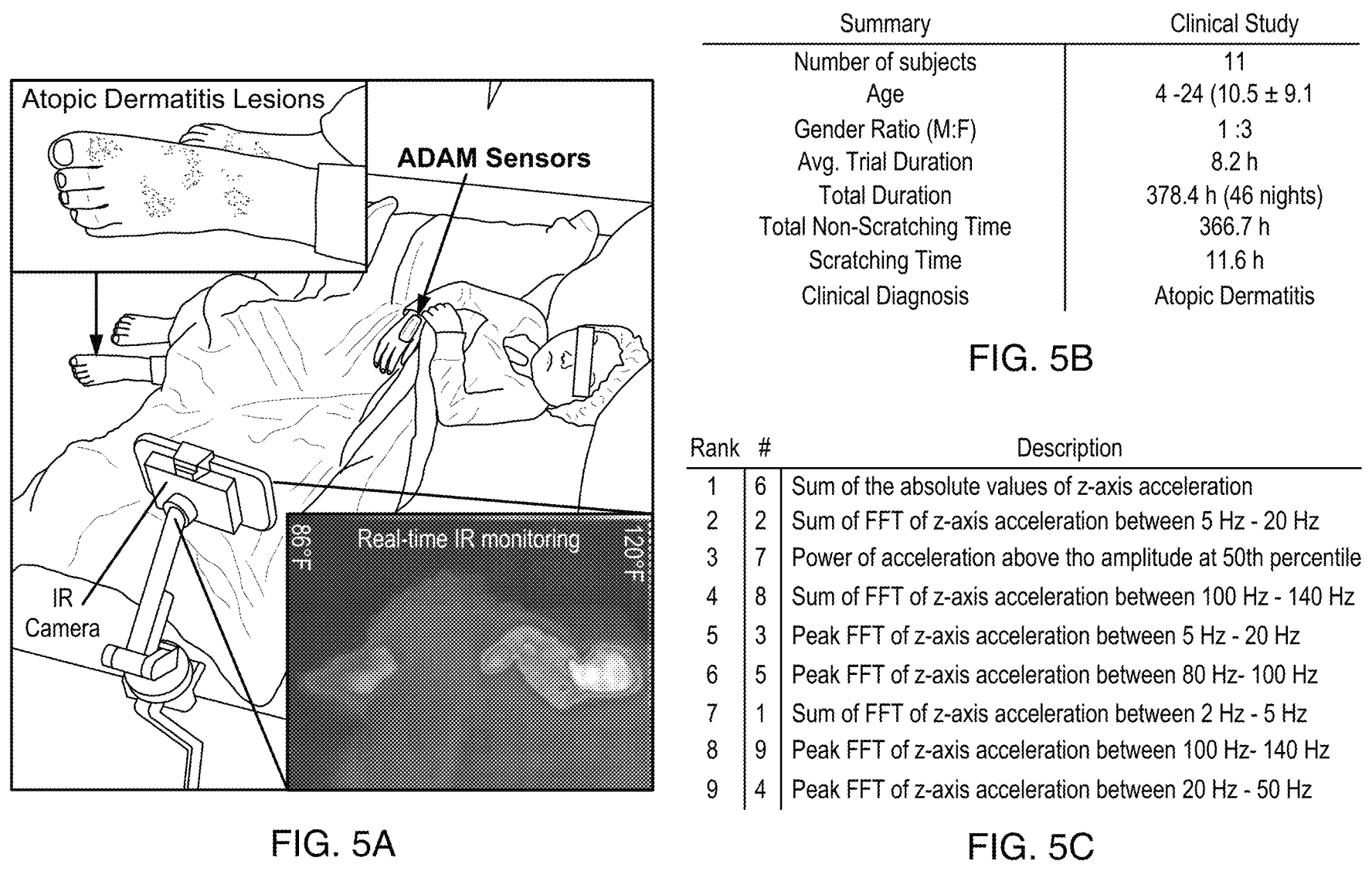

| Summary | Clinical Study |
|---|---|
| Number of subjects | 11 |
| Age | 4 -24 (10.5 ± 9.1 |
| Gender Ratio (M:F) | 1 :3 |
| Avg. Trial Duration | 8.2 h |
| Total Duration | 378.4 h (46 nights) |
| Total Non-Scratching Time | 366.7 h |
| Scratching Time | 11.6 h |
| Clinical Diagnosis | Atopic Dermatitis |

FIG. 5B

| Rank | # | Description |
|---|---|---|
| 1 | 6 | Sum of the absolute values of z-axis acceleration |
| 2 | 2 | Sum of FFT of z-axis acceleration between 5 Hz - 20 Hz |
| 3 | 7 | Power of acceleration above tho amplitude at 50th percentile |
| 4 | 8 | Sum of FFT of z-axis acceleration between 100 Hz - 140 Hz |
| 5 | 3 | Peak FFT of z-axis acceleration between 5 Hz - 20 Hz |
| 6 | 5 | Peak FFT of z-axis acceleration between 80 Hz- 100 Hz |
| 7 | 1 | Sum of FFT of z-axis acceleration between 2 Hz - 5 Hz |
| 8 | 9 | Peak FFT of z-axis acceleration between 100 Hz- 140 Hz |
| 9 | 4 | Peak FFT of z-axis acceleration between 20 Hz - 50 Hz |

FIG. 5C

ACOUSTO-MECHANIC SENSORS AND APPLICATIONS OF SAME

CROSS-REFERENCE TO RELATED PATENT APPLICATION

This application claims priority to and the benefit of U.S. Provisional Application Ser. No. 63/171,483, filed Apr. 6, 2021, which is incorporated herein by reference in its entirety.

STATEMENT AS TO RIGHTS UNDER FEDERALLY-SPONSORED RESEARCH

This invention was made with government support under Grant No. 1U01FD007001-01 awarded by the Food and Drug Administration. The government has certain rights in the invention.

FIELD OF THE INVENTION

The present invention relates generally to biosensors, and more particularly to skin-conformable, wireless, dual wearable diagnostic and therapeutic scratch sensors enabled by machine learning algorithms for assessing specific signatures of scratching, methods for quantifying symptoms of pruritus, and applications of the same.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Itch and pain are the two cardinal examples of nociception in humans—itch leads to a scratch reflex while pain leads to a withdrawal reflex. Unfortunately, itch is often overlooked and undertreated in the clinical setting in spite of the wide range of medical conditions that cause itch—1% of all outpatient visits yearly involve the symptom of itch, as a significant global disease burden. While a wide range of medical conditions leads to itch (e.g., renal failure, liver failure, lymphoma), atopic dermatitis (AD) is likely the most common. AD is also the most widespread pediatric inflammatory skin disease, affecting 10 million US children with a yearly prevalence of 13%. The hallmark of AD is itch, the primary driver of morbidity that leads to chronic sleep disturbance in ~60% of affected children. The consequences for millions of children include neurocognitive impairment and decreased growth. The quality of life of patients with moderate-to-severe AD consistently scores among the lowest of all chronic diseases.

In AD and other conditions that cause itch, a major unmet need is in objective measures of itch to assess the efficacy of new medications, quantify disease severity, and monitor treatment response. The subjective nature of itch creates difficulties in its quantification. Commonly used methods such as patient reported visual analogue scales (VAS) poorly correlate to visually observed scratching behavior. Such self-reported measures are also prone to both sensitivity and anchoring bias. Furthermore, these subjective methods lack validity in young children and cognitively impaired adults.

Measuring behaviors associated with scratching provides one method to quantify itch severity and frequency. Direct visual inspection of scratching in video recordings represents the gold standard, but such schemes are both labor intensive and impractical in clinical practice. Wrist actigraphy, a method to record movements using accelerometers, estimates scratching by measuring wrist motion. This approach offers sub-optimal accuracy due to an inability to distinguish, for example, hand-waving from scratching. Additional aspects of the widely varying characteristics of scratching, including variabilities across individuals, represent additional unsolved challenges. Thus, current sensors and strategies do not offer sufficient performance or practicality for routine use in clinical trials or patient care.

Therefore, a heretofore unaddressed need exists in the art to address the aforementioned deficiencies and inadequacies.

SUMMARY OF THE INVENTION

One of the objectives of this invention is to disclose a soft, flexible, and wireless sensor capable of capturing acousto-mechanic signatures of scratching and methods for objectively quantifying symptoms of pruritus.

In one aspect, the invention relates to an advanced acousto-mechanic (ADAM) sensor comprising at least one inertial measurement unit (IMU) for operably detecting vibratory and motion signatures of physiological processes; and a plurality of electronic components comprising a microcontroller unit (MCU) coupled to the at least one IMU for receiving data from the at least one IMU and processing the received data, and a wireless communication system for wireless data transmission. The acousto-mechanic sensor is configured to measure signals of both low frequency less than about 100 Hz and high frequency greater than about 100 Hz derived from the at least one IMU. Further, the acousto-mechanic sensor is skin mounted to allow for coupling of the at least one IMU to the skin for capture of both the high frequency and low frequency signals. he high frequency and low frequency signals are representative of a physiological response to itch as a scratching or rubbing activity. In one embodiment, the physiological processes comprise scratching activities.

In one embodiment, the plurality of electronic components and the at least one IMU are spatially separated so that the plurality of electronic components is in one end of the ADAM sensor and the at least one IMU is in the other end of the ADAM sensor.

In one embodiment, the ADAM sensor further comprises a flexible printed circuit board (fPCB) for supporting and interconnecting the at least one IMU and the plurality of electronic components.

In one embodiment, the fPCB adopts a patterned layout that includes a plurality of freely deformable, serpentine interconnects, designed to mechanically decouple the at least one IMU from the other components of the ADAM sensor.

In one embodiment, the plurality of freely deformable, serpentine interconnects is flexible and stretchable and adapted for interconnecting the at least one IMU and the plurality of electronic components.

In one embodiment, the ADAM sensor also comprises an elastomeric encapsulation layer at least partially surrounding the at least one IMU, the plurality of electronic components and the fPCB to form a tissue-facing surface operably attached to the living subject.

In one embodiment, the tissue-facing surface of the elastomeric encapsulation layer is configured to conform to a skin surface of the living subject.

In one embodiment, the encapsulation layer is formed of a thin, low modulus silicone elastomer.

In one embodiment, the elastomeric encapsulation layer is a biocompatible silicone enclosure.

In one embodiment, the ADAM sensor further comprises a biocompatible hydrogel adhesive for attaching the ADAM sensor on an anatomical location of a living subject.

In one embodiment, the biocompatible hydrogel adhesive is a medical-grade, hypoallergenic adhesive.

In one embodiment, the biocompatible hydrogel adhesive is adapted such that signals from the living subject are operably conductible to the at least one IMU.

In one embodiment, the wireless communication system comprises a Bluetooth low energy (BLE) radio.

In one embodiment, the wireless communication system is configured to send an output signal from the ADAM sensor to an external device.

In one embodiment, in the plurality of electronic components further comprises a power module coupled to the at least one IMU, the wireless communication system and the MCU for providing power thereto.

In one embodiment, the power module comprises a battery.

In one embodiment, the battery is a rechargeable battery.

In one embodiment, the power module further comprises a wireless charging module for wirelessly charging the rechargeable battery.

In one embodiment, the power module further comprises a failure prevention element including a short-circuit protection component or a circuit to avoid battery malfunction.

In one embodiment, the at least one IMU comprises a millimeter-scale, three-axis accelerometer configured to detect skin-conducted vibrations and motions associated with scratching activities.

In one embodiment, the three-axis accelerometer is configured to detect acceleration along the x-axis and y-axis at a first sample rate, and acceleration along the z-axis at a second sample rate, wherein the x-axis and y-axis are oriented parallel to a skin surface on which the ADAM sensor is attached, and the z-axis is perpendicular to the skin surface.

In one embodiment, the first sample rate is in a range of 160-240 Hz, and the second sample rate is in a range of 1,200-2,000 Hz.

In one embodiment, the three-axis accelerometer is configured to have a sampling rate of 1,600 Hz at a resolution of 16 bits and a dynamic range of ±2g, wherein g is the gravitational acceleration, 9.8 m/s$^2$.

In one embodiment, when placed on the dorsum of the hand, the ADAM sensor is able to detect acousto-mechanic signals associated with the scratching activities via a combination of motion and acousto-mechanic signals, in a manner that is immune to ambient noise.

In one embodiment, when placed between the second and third finger meta-carpal bones, the ADAM sensor is able to quantify the scratching activities initiated not only from motions of the wrist and/or arm, but from the fingers and fingertips as well, across a wide temporal bandwidth that includes high frequency vibratory motions associated with scratching itself.

In one embodiment, the scratching activities are characterized with first and second types of signals, wherein the first type of signals corresponds to gross movements of the hand, and the second type of signals, overlapping in time with the first type of signals, arises from subtle vibratory impulses generated by motions of the fingertips and fingernails against a contacting surface.

In one embodiment, the first type of signals has characteristic frequencies in the range of a few Hz or less, and the second type of signals has characteristic frequencies extending into the range of a few hundred Hz and amplitudes decaying rapidly with position along the fingers and into the hand, and eventually passing through the wrist and to the arm.

In one embodiment, the first and second types of signals are identified by passing the data through low pass and high pass filters with cutoffs at 2 Hz.

In one embodiment, signatures of acousto-mechanic signal features that uniquely characterize the scratching activities are extracted from the output signals of the ADAM sensor to train and validate a machine learning-based algorithm for scratch detection so as to quantify symptoms of pruritus.

In one embodiment, the ADAM sensor is load-free, stretchable, twistable, and/or bendable.

In one embodiment, the ADAM sensor is flexible and conformable to the skin with a specific geometrical polarity for mounting in an anatomical location of the living subject.

In one embodiment, scratch algorithms are embedded on the sensor such that the sensor is capable of processing the data detected from the at least one IMU to obtain signal features that uniquely characterize the scratching activities.

In one embodiment, the ADAM sensor is configured to notify the user and/or professionals, via audio/visual means of the acousto-mechanic sensor, mobile devices, and/or smart wearable devices. These notifications may be strong enough to generate attention to scratching by users—or tunable to be more gentle so as to stop scratching at sleep but not wake up the wearer.

In one embodiment, conformability of the sensor on the hand allows placement over key bones—e.g. the metatarsals of the 1$^{st}$ and 2$^{nd}$ digit—which is key to capture high frequency vibrations that are specific to scratching.

In one embodiment, high frequency signal capture enabled by the high frequency IMU allows for capture of both motion and bone-conducted high frequency vibrations that are specific for scratching. This allows us to differentiate the motion of scratching from true scratching on the skin.

In one embodiment, the low profile conformable nature of the sensor allows placement of the acousto-mechanic sensor on the curvilinear surface of the dorsal hand. This allows capture of scratching no matter the articulation of the joint. Said scratching can be associated with finger movements only, wrist movements only, elbow movements only, shoulder movements only, or a combination of them.

In one embodiment, the ADAM sensor is operably placed on the dorsum of the hand, finger nail, finger, or wrist, for measuring scratching motions of any time.

In one embodiment, the ADAM sensor is usable in any condition where itch is a symptom as a diagnosis, treatment response indicator, clinical trials endpoint, or early warning of worsening disease.

In another aspect, the invention relates to a method for quantifying symptoms of pruritus, comprising attaching an advanced acousto-mechanic (ADAM) sensor to an anatomical location of a living subject; detecting, by the ADAM sensor, signals associated with scratching and/or non-scratching activities; and analyzing the signals to evaluate acousto-mechanic signatures of scratching so as to quantify symptoms of pruritus.

In one embodiment, said analyzing the signals comprises preprocessing the signals to remove low frequency baseline wandering caused by slow, large-scale motions, so that the preprocessed signals contain more specific high frequency signal components associated with z-axis acceleration; segmenting the preprocessed signals into frames by sliding a n-second window with an overlap; extracting a set of features from each frame; and applying a random forest (RF) classifier to the set of extracted features for prediction and validation. In one embodiment, the set of features comprises variability of acceleration in x/y/z axis, high frequency spectrogram, and/or low frequency spectrogram.

In one embodiment, the n-second window is a 1-second window.

In one embodiment, the overlap is in a range of about 50%-90% overlap, preferably about 50%.

In one embodiment, said analyzing the signals further comprises assigning each frame a label of 0 that indicates non-scratching activity, if less than about 50% of data points in a given frame are labeled as scratching activity, otherwise, assigning the frame a label of 1 that indicates scratching activity.

In one embodiment, the RF classifier is trained with a training data set that contains scratching data from a plurality of body locations and various types of non-scratching activities collected from a number of healthy living subjects.

In one embodiment, the RF classifier is optimized by comparing results from leave-one-subject-out cross validation (LOSO-CV) applied to the training data set, wherein the results form the basis for optimization of the RF classifier.

In one embodiment, parameters for the optimization comprises a number of decision trees in the RF classifier and a minimum required scratching (MRS) duration.

In one embodiment, the number of decision trees is in a range from about 10 to 200, preferably, about 30.

In one embodiment, for the optimization, the RF classifier returns predictions at a 1-second frame level, and the outputs are subsequently clustered using density-based spatial clustering of applications with noise (DBSCAN), so as to join two scratching frames in close proximity as a single scratching event, wherein the MRS duration defines the minimum number of frames to form a cluster of scratching events.

In one embodiment, the MRS duration is in a range from about 1.5 to 8.5 seconds, preferably, at least about 4.5 seconds.

In one embodiment, the scratching and/or non-scratching activities comprises scratching at the head, the arm, the abdomen, the knee and/or the leg of the living subject, and/or simulating scratching in the air, hand waving, texting on the phone, typing on a keyboard, and/or clicking a mouse.

In one embodiment, the anatomical location is at the fingertip, finger, dorsum of the hand, and the wrist of the living subject.

Yet another aspect of the invention relates to a non-transitory tangible computer-readable medium storing instructions which, when executed by one or more processors, cause the above disclosed method for quantifying symptoms of pruritus.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

FIG. 1A: Image of the ADAM sensor in in various states of deformation to highlight its soft, flexible construction. FIG. 1B: Results of measurements of spatio-temporal patterns of motions and vibratory signatures of scratching, with a focus on five different frequency ranges. The experiments involve four accelerometers, one each located at the fingertip, finger, dorsum of the hand, and the wrist, during scratching by articulating the arm for 10 s and then scratching with only the finger for the last 10 s. The color bars represent the mean power of the signal per frequency in each frequency band. The left and right values indicate the minimum and maximum of the respective plot. Upper spatial patterns are from scratching by articulating the arm and lower spatial patterns are from scratching with only the finger. FIG. 1C: Path of scratching and resulting data (raw and filtered) data from the sensor. FIG. 1D: Comparison of signals captured during scratching with five different mounting locations, as time series and spectrogram plots. The dorsal hand is an effective mounting location for capturing scratching with only the fingers.

FIG. 2A: Sample time-series data and spectrogram corresponding to scratching activities. Two modes of scratching are conducted on two body parts, dorsum of the hand (DH) and forearm (FA), in two intensities of high (H) and low (L). FIG. 2B: Time series data of scratching activity in which 5 different body parts include head (hairy skin), arm (normal skin), abdomen (soft skin), knee (bony prominence skin), and the leg (hard skin). FIG. 2C: The spectrogram of each time series data in FIG. 2B. The signal due to the scratching activities have the energy in the 0-800 Hz frequency range. FIG. 2D: Time series data in a wide range of non-scratching activities including simulated moving fingers in the air, waving hand, text messaging, typing the keyboard, and clicking the mouse. FIG. 2E: The spectrogram of each time series data in FIG. 2D. The signals due to non-scratching activities have energy mainly in the range less than 200 Hz.

FIG. 3A: Scratching by articulating the whole wrist. The 'ItchTracker' misclassifies hand waving as scratching and fails to detect scratching on the head. FIG. 3B: Scratching by articulating only the fingers. The ADAM sensor reliably discriminates scratching the skin using only articulation of the fingers. The 'ItchTracker' cannot detect scratches using only fingers, given its mounting location on the wrist and its inability to record high frequency information.

FIG. 4A: The algorithm validation data was collected from 10 healthy normal volunteers. FIG. 4B: Activities performed by each participant and their corresponding activity durations. FIG. 4C: Preprocessing subsequently applied to the sets, and segmented into frames by applying a sliding window of 1 s. From each frame, a set of features were extracted. With the feature set extracted from the training frames, a random forest classifier was trained. The trained classifier was applied to the test feature set for prediction and validation. FIG. 4D: Time series data of our validation cohort with a single subject performing various scratching and non-scratching activities include 5 s pause periods between each activity. FIG. 4E: The output probability for scratching is characterized as "1: scratch" if the probability exceeds 50%. The blue line is the probability of scratching for each frame and the red line indicates the final classified result, where 0 and 1 correspond to non-scratch and scratch, respectively.

FIGS. 5A-5C show validation data summary and extracted features according to embodiments of the invention. FIG. 5A: The clinical validation was conducted in a natural home environment with predominately pediatric atopic dermatitis patients (median age 10.5 years). An infrared IR camera was used to record scratching behavior of human subjects and was manually graded by 2 clinical research staff members. FIG. 5B: A total of 11 AD patients were recruited generating a total of 46 nights of data in a pooled analysis. FIG. 5C: A total of 9 features were used for LOSO and cross study validation. They are listed in order of their feature importance obtained from random forest classifier.

FIG. 6A: Power dissipation from the fingertips to the wrist determined using four devices and two devices. The devices on the finger and hand have no effect on the attenuation between the fingertip and the wrist. FIG. 6B: Power dissipation from the dorsum of the hand to the wrist. Results of attenuation along the sensor attached location using 4 sensors in FIG. 1B are consistent with those in FIG. 1D. FIG. 6C: Power law frequency and distance dependent acoustic attenuation, $P(x+\Delta x)=P(x)\exp(-\alpha_0 f^\eta \Delta x)$.

FIG. 8A: Scratching the dorsum of the hand (DH) by articulating the arm. FIG. 8B: Scratching the forearm (FA) by articulating the arm. FIG. 8C: Scratching the DH with only the fingers. FIG. 8D: Scratching the FA with only the fingers.

DETAILED DESCRIPTION OF THE INVENTION

Figures 1A, 1B:
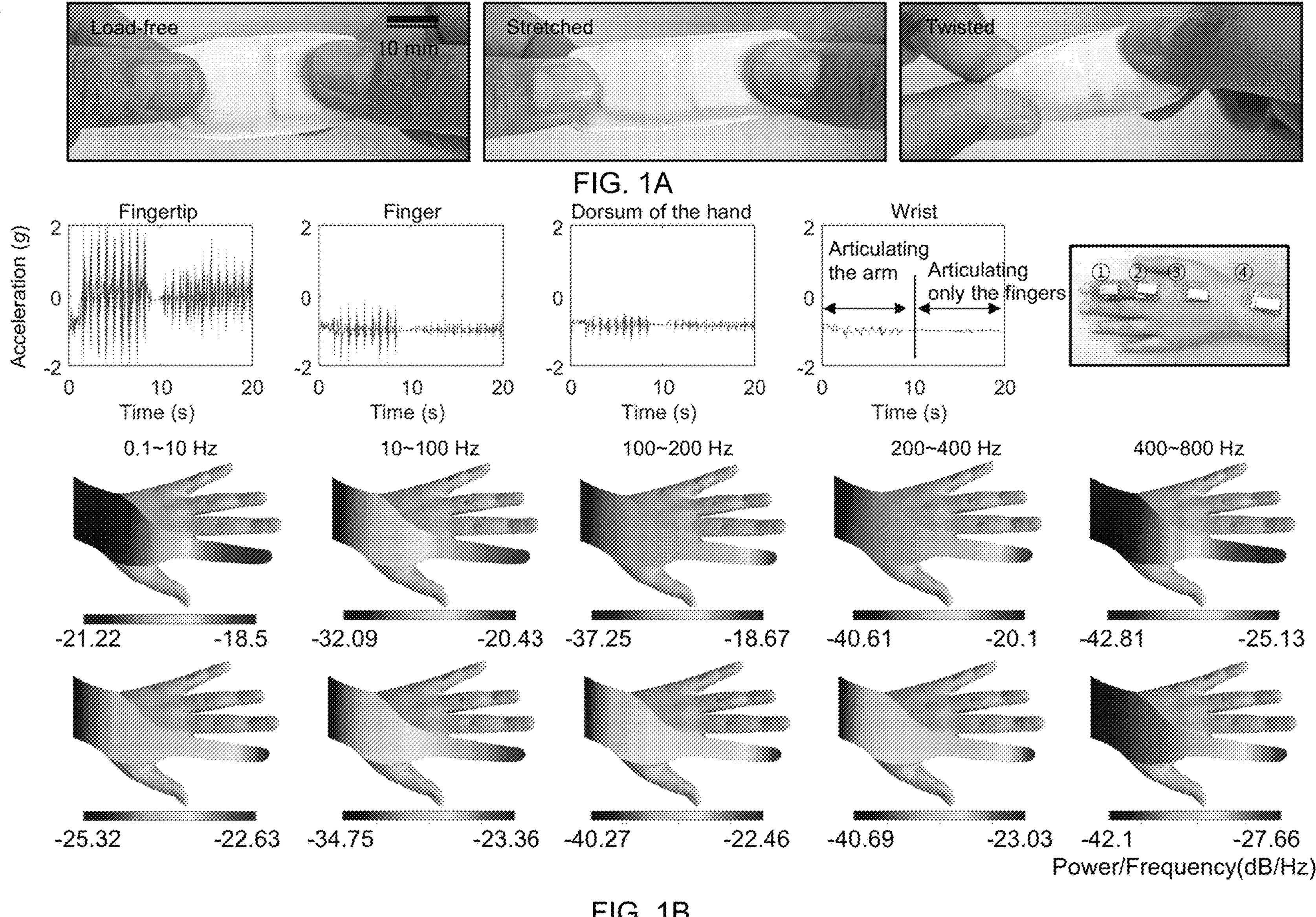
FIGS. 1A-1D show overview of the ADAM sensor and signal outputs according to embodiments of the invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed may be resorted to by those skilled in the art, and that such modifications and variations are considered to be within the scope of this invention as defined by the appended claims.

Whenever a range is given in the specification, for example, a temperature range, a time range, or a composition or concentration range, all intermediate ranges and subranges, as well as all individual values included in the ranges given are intended to be included in the invention. It will be understood that any subranges or individual values in a range or subrange that are included in the description herein can be excluded from the claims herein.

It will be understood that, as used in the description herein and throughout the claims that follow, the meaning of "a", "an", and "the" includes plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising", or "includes" and/or "including", or "has" and/or "having", or "carry" and/or "carrying", or "contain" and/or "containing", or "involve" and/or "involving", "characterized by", and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

As used in the disclosure, "around", "about", "approximately" or "substantially" shall generally mean within 20 percent, preferably within 10 percent, and more preferably within 5 percent of a given value or range. Numerical quantities given herein are approximate, meaning that the term "around", "about", "approximately" or "substantially" can be inferred if not expressly stated.

As used in the disclosure, the phrase "at least one of A, B, and C" should be construed to mean a logical (A or B or C), using a non-exclusive logical OR. As used herein, the term "and/or" includes any and all combinations of one or more of the associated listed items.

As used in the disclosure, the term "wireless communication system" refers to onboard components of sensors, wireless controller and other electronic components that provides capability of receiving and sending signals using at least one communication protocol of near field communication (NFC), Wi-Fi/Internet, Bluetooth, Bluetooth low energy (BLE), and Cellular communication protocols for wireless communication. In this manner, an output may be provided to an external device, including a cloud-based device, personal portable device, or a caregiver's computer system. Similarly, a command may be sent to the sensor, such as by an external controller, which may or may not correspond to the external device. Machine learning algorithms may be employed to improve signal analysis and, in turn, command signals sent to the medical sensor, including a stimulator of the medical sensor for providing haptic signal to a user of the medical device useful in a therapy. More generally, these systems may be incorporated into a processor, such as a microprocessor located on-board or physically remote from the electronic device of the medical sensor. An example of the wireless controller is a near field communication (NFC) chip, including NFC chips. NFC is a radio technology enabling bi-directional short range wireless communication between devices. Another example of a wireless controller is a Bluetooth® chip, or a BLE system-on-chip (SoC), which enables devices to communicate via a standard radio frequency instead of through cables, wires or direct user action.

As used in the disclosure, the term "conformable" refers to the ability of a device to undergo macroscopic deformation so as to maintain intimate contact with a curvilinear surface without generating substantial deformation forces on the underlying surface. Such conformal contact is particularly challenging in the context of soft biological tissue that is readily deformed, even under relatively mild forces, including the skin. Such unwanted deformation-generating forces can cause discomfort and irritation to the underlying tissue. Such problems are avoided in the instant technology by specially constructing the penetrating members, optical sources, and supporting substrate, so that the device as a whole is flexible and able to accommodate a wide range of complex shapes, thereby ensuring conformal contact is maintained. Such conformal contact may be further quantified in terms of no significant separation distance between the device and underlying surface. This helps ensure maximum light delivery to the desired location, and avoids unwanted light leakage. Conformability may also be described in terms of the device being "flexible" and having a suitable bending modulus to provide desired curvature under an applied force. Conformable may be further described in terms of desired mechanical properties such as bending stiffness and Young's modulus such that air gaps are not present, thereby maximizing light transfer to underlying tissue.

The term "flexibility" or "bendability", as used in the disclosure, refers to the ability of a material, structure, device or device component to be deformed into a curved or bent shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. A used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 100 microns, optionally less than 10 microns and optionally less than 1 micron) and device geometries such as thin film and open or mesh geometries.

The term "bending stiffness" refers to a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

The term "elastomer", as used in the disclosure, refers to a polymeric material which can be stretched or deformed and return to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers useful include, but are not limited to, thermoplastic elastomers, styrenic materials, olefenic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. Exemplary elastomers include, but are not limited to, silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefenic materials, polyolefin, polyurethane thermoplastic elastomers, polyamides, synthetic rubbers, polyisobutylene, poly(styrene-butadiene-styrene), polyurethanes, polychloroprene and silicones. In one embodiment, a flexible polymer is a flexible elastomer.

The term "encapsulate" or "encapsulation", as used in the disclosure, refers to the orientation of one structure such that it is at least partially, and in some cases completely, surrounded by one or more other structures. "Partially encapsulated" refers to the orientation of one structure such that it is partially surrounded by one or more other structures. "Completely encapsulated" refers to the orientation of one structure such that it is completely surrounded by one or more other structures. The invention includes devices having partially or completely encapsulated electronic devices, device components and/or inorganic semiconductor components.

Embodiments of the invention are illustrated in detail hereinafter with reference to accompanying drawings. The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

Measuring behaviors associated with scratching provides one method to quantify itch severity and frequency. Direct visual inspection of scratching in video recordings represents the gold standard, but such schemes are both labor intensive and impractical in clinical practice. Wrist actigraphy, a method to record movements using accelerometers, estimates scratching by measuring wrist motion, which offers sub-optimal accuracy due to an inability to distinguish, for example, hand-waving from scratching. Additional aspects of the widely varying characteristics of scratching, including variabilities across individuals, represent additional unsolved challenges. Thus, existing sensors and strategies do not offer sufficient performance or practicality for routine use in clinical trials or patient care.

This invention, among other things, discloses a strategy that exploits a soft, flexible, wireless, and low-profile sensor capable of capturing both vibratory and motion signatures of physiological processes with clinical grade data quality. This device, which is also referred as the ADAM (ADvanced Acousto-Mechanic) sensor, softly couples to the skin to enable capture of both low frequency (e.g., motion) and high frequency (acousto-mechanic) signals from the human body. An embedded rechargeable battery allows for seven days of continuous operation on a single wireless charge. When placed on the dorsum of the hand, the ADAM sensor is able to capture acousto-mechanic signals associated with scratching via a combination of motion and acousto-mechanic signals, in a manner that is immune to ambient sounds of any type. Specifically, when placed between the second and third finger meta-carpal bones, the ADAM sensor can quantify scratching behavior initiated not only from motions of the wrist and/or arm, but from the fingers and fingertips as well, across a wide temporal bandwidth that includes high frequency vibratory motions associated with scratching itself. Using the sensor data and an associated understanding of the physics of the processes of scratching, signal features that uniquely characterize scratching activities can be extracted to train and validate a machine learning-based algorithm for scratch detection.

In one aspect of the invention, the ADAM sensor includes at least one inertial measurement unit (IMU) for operably detecting vibratory and motion signatures of physiological processes; and a plurality of electronic components comprising a microcontroller unit (MCU) coupled to the at least one IMU for receiving data from the at least one IMU and processing the received data, and a wireless communication system for wireless data transmission. The acousto-mechanic sensor is configured to measure signals of both low frequency less than about 100 Hz and high frequency greater than about 100 Hz derived from the at least one IMU. Further, the acousto-mechanic sensor is skin mounted to allow for coupling of the at least one IMU to the skin for capture of both the high frequency and low frequency signals. he high frequency and low frequency signals are representative of a physiological response to itch as a scratching or rubbing activity. In one embodiment, the physiological processes comprise scratching activities.

In one embodiment, the plurality of electronic components and the at least one IMU are separated so that the plurality of electronic components is in one end of the ADAM sensor and the at least one IMU is in the other end of the ADAM sensor.

In one embodiment, the ADAM sensor is load-free, stretchable, twistable, and/or bendable. In one embodiment, the ADAM sensor is flexible and conformable to the skin with a specific geometrical polarity for mounting in an anatomical location of a living subject.

In one embodiment, the at least one IMU comprises a millimeter-scale, three-axis accelerometer configured to detect skin-conducted vibrations and motions associated with scratching activities. In one embodiment, the three-axis accelerometer is configured to detect acceleration along the x-axis and y-axis at a first sample rate, and acceleration along the z-axis at a second sample rate, wherein the x-axis and y-axis are oriented parallel to a skin surface on which the ADAM sensor is attached, and the z-axis is perpendicular to the skin surface. In one embodiment, the first sample rate is in a range of about 160-240 Hz, and the second sample rate is in a range of about 1,200-2,000 Hz. In one embodiment, the three-axis accelerometer is configured to have a sampling rate of about 1,600 Hz at a resolution of 16 bits and a dynamic range of about ±2g, wherein g is the gravitational acceleration, 9.8 $m/s^2$.

In one embodiment, the ADAM sensor further comprises a flexible printed circuit board (fPCB) for supporting and interconnecting the at least one IMU and the plurality of electronic components. In one embodiment, the fPCB adopts a patterned layout that includes a plurality of freely deformable, serpentine interconnects, designed to mechanically decouple the at least one IMU from the other components of the ADAM sensor. In one embodiment, the plurality of freely deformable, serpentine interconnects is flexible and stretchable and adapted for interconnecting the at least one IMU and the plurality of electronic components.

In one embodiment, the ADAM sensor also comprises an elastomeric encapsulation layer at least partially surrounding the at least one IMU, the plurality of electronic components and the fPCB to form a tissue-facing surface operably attached to the living subject. In one embodiment, the tissue-facing surface of the elastomeric encapsulation layer is configured to conform to a skin surface of the living subject. In one embodiment, the encapsulation layer is formed of a thin, low modulus silicone elastomer. In one embodiment, the elastomeric encapsulation layer is a biocompatible silicone enclosure.

In one embodiment, the ADAM sensor further comprises a biocompatible hydrogel adhesive for attaching the ADAM sensor on an anatomical location of a living subject. In one embodiment, the biocompatible hydrogel adhesive is a medical-grade adhesive.

In one embodiment, the wireless communication system comprises a Bluetooth low energy (BLE) radio. In one embodiment, the wireless communication system is configured to send an output signal from the ADAM sensor to an external device.

In one embodiment, in the plurality of electronic components further comprises a power module coupled to the at least one IMU, the wireless communication system and the MCU for providing power thereto. In one embodiment, the power module comprises a battery. In one embodiment, the battery is a rechargeable battery. In one embodiment, the power module further comprises a wireless charging module for wirelessly charging the rechargeable battery. In one embodiment, the power module further comprises a failure prevention element including a short-circuit protection component or a circuit to avoid battery malfunction.

In one embodiment, when placed on the dorsum of the hand, the ADAM sensor is able to detect acousto-mechanic signals associated with the scratching activities via a combination of motion and acousto-mechanic signals, in a manner that is immune to ambient noise. In one embodiment, when placed between the second and third finger meta-carpal bones, the ADAM sensor is able to quantify the scratching activities initiated not only from motions of the wrist and/or arm, but from the fingers and fingertips as well, across a wide temporal bandwidth that includes high frequency vibratory motions associated with scratching itself.

In one embodiment, the scratching activities are characterized with first and second types of signals, wherein the first type of signals corresponds to gross movements of the hand, and the second type of signals, overlapping in time with the first type of signals, arises from subtle vibratory impulses generated by motions of the fingertips and fingernails against a contacting surface. In one embodiment, the first type of signals has characteristic frequencies in the range of a few Hz or less, and the second type of signals has characteristic frequencies extending into the range of a few hundred Hz and amplitudes decaying rapidly with position along the fingers and into the hand, and eventually passing through the wrist and to the arm. In one embodiment, the first and second types of signals are identified by passing the data through low pass and high pass filters with cutoffs at 2 Hz.

In one embodiment, signal features that uniquely characterize the scratching activities are extracted from the output signals of the ADAM sensor to train and validate a machine learning-based algorithm for scratch detection so as to quantify symptoms of pruritus.

In one embodiment, the ADAM sensor is operably placed on the dorsum of the hand, finger nail, finger, or wrist, for measuring scratching motions of any time.

In one embodiment, the ADAM sensor is usable in any condition where itch is a symptom as a diagnosis, treatment response indicator, clinical trials endpoint, or early warning of worsening disease.

In another aspect of the invention, the method for quantifying symptoms of pruritus, includes attaching an advanced acousto-mechanic (ADAM) sensor to an anatomical location of a living subject; detecting, by the ADAM sensor, signals associated with scratching and/or non-scratching activities; and analyzing the signals to evaluate acousto-mechanic signatures of scratching so as to quantify symptoms of pruritus.

In one embodiment, said analyzing the signals comprises preprocessing the signals to remove low frequency baseline wandering caused by slow, large-scale motions, so that the preprocessed signals contain more specific high frequency signal components associated with z-axis acceleration; segmenting the preprocessed signals into frames by sliding a n-second window with an overlap; extracting a set of features from each frame; and applying a random forest (RF) classifier to the set of extracted features for prediction and validation. In one embodiment, the n-second window is a 1-second window. In one embodiment, the overlap is in a range of about 50%-90% overlap, preferably about 50%.

In one embodiment, said analyzing the signals further comprises assigning each frame a label of 0 that indicates non-scratching activity, if less than about 50% of data points in a given frame are labeled as scratching activity, otherwise, assigning the frame a label of 1 that indicates scratching activity.

In one embodiment, the RF classifier is trained with a training data set contains scratching data from a plurality of body locations and various types of non-scratching activities collected from a number of healthy living subjects.

In one embodiment, the RF classifier is optimized by comparing results from leave-one-subject-out cross validation (LOSO-CV) applied to the training data set, wherein the results form the basis for optimization of the RF classifier.

In one embodiment, parameters for the optimization comprises a number of decision trees in the RF classifier and a minimum required scratching (MRS) duration.

In one embodiment, the number of decision trees is in a range from about 10 to 200, preferably, about 30.

In one embodiment, for the optimization, the RF classifier returns predictions at a 1-second frame level, and the outputs are subsequently clustered using density-based spatial clustering of applications with noise (DBSCAN), so as to join two scratching frames in close proximity as a single scratching event, wherein the MRS duration defines the minimum number of frames to form a cluster of scratching events.

In one embodiment, the MRS duration is in a range from about 1.5 to 8.5 seconds, preferably, at least about 4.5 seconds.

In one embodiment, the scratching and/or non-scratching activities comprises scratching at the head, the arm, the abdomen, the knee and/or the leg of the living subject, and/or simulating scratching in the air, hand waving, texting on the phone, typing a keyboard, and/or clicking a mouse.

In one embodiment, the anatomical location is at the fingertip, finger, dorsum of the hand, and the wrist of the living subject.

It should be noted that all or a part of the steps according to the embodiments of the invention is implemented by hardware or a program instructing relevant hardware.

Yet another aspect of the invention provides a non-transitory tangible computer-readable medium storing instructions which, when executed by one or more processors, cause the above disclosed method for quantifying symptoms of pruritus. The computer executable instructions or program codes enable the above disclosed apparatus or a similar system to complete various operations in accordance with the above disclosed method. The storage medium/memory may include, but is not limited to, high-speed random access medium/memory such as DRAM, SRAM, DDR RAM or other random access solid state memory devices, and non-volatile memory such as one or more magnetic disk storage devices, optical disk storage devices, flash memory devices, or other non-volatile solid state storage devices.

According to the invention, the non-invasive technology can objectively quantify scratching behavior via a soft, flexible, and wireless sensor that captures the acousto-mechanic signatures of scratching from the dorsum of the hand. Using the sensor data and an associated understanding of the physics of the processes of scratching, signal features that uniquely characterize scratching activities can be extracted to train and validate a machine learning-based algorithm for scratch detection.

In addition, clinical validation in a cohort of predominately pediatric patients (n=11) with moderate to severe atopic dermatitis included 46 sleep-nights totaling 378.4 hours. The data indicate an accuracy of about 99.0% (about 84.3% sensitivity, about 99.3% specificity) against visual observation. This work suggests broad capabilities relevant to applications ranging from the assessing the efficacy of drugs for conditions that cause itch, to monitoring disease severity and treatment response.

These and other aspects of the present invention are further described below. Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

EXAMPLE

Skin-Conformable Wireless Sensor to Objectively Quantify Symptoms of Pruritus In this exemplary study, we develop a strategy that exploits a soft, flexible, wireless, and low-profile sensor capable of capturing both vibratory and motion signatures of physiological processes with clinical grade data quality. This device, also referred in the disclosure as the ADAM (ADvanced Acousto-Mechanic) sensor, softly couples to the skin to enable capture of both low frequency (e.g., motion) and high frequency (acousto-mechanic) signals from the human body. An embedded rechargeable battery allows for seven days of continuous operation on a single wireless charge. When placed on the dorsum of the hand, the ADAM sensor is able to capture acousto-mechanic signals associated with scratching via a combination of motion and acousto-mechanic signals, in a manner that is immune to ambient noise. Specifically, when placed between the second and third finger meta-carpal bones, the ADAM sensor can quantify scratching behavior initiated not only from motions of the wrist and/or arm, but from the fingers and fingertips as well, across a wide temporal bandwidth that includes high frequency vibratory motions associated with scratching itself. Using the sensor data and an associated understanding of the physics of the processes of scratching, signal features that uniquely characterize scratching activities can be extracted to train and validate a machine learning-based algorithm for scratch detection.

The content begins with descriptions of systematic investigations of the mechanics of scratching in a set of controlled experiments, followed by validation of the combined use of sensor signals with data analytics approaches in two human subject studies: an algorithm development study (n=10 healthy normal subjects) and a clinical validation study (n=11 predominately pediatric patients with AD). The training study involves collection of scratching and non-scratching datain well-defined conditions to develop a machine-learning (ML) algorithm to categorize and quantify scratching behavior. The clinical study validates the sensor and the algorithm in a cohort of patients with moderate to severe AD. The performance compares well to a gold standard defined by direct visual observation via manually labeled IR camera recordings.

Study Design

Two data sets were collected independently for model development (training) and validation. The training data, collected in a controlled environment, served as the basis for developing an ML algorithm for detecting scratching behavior. The validation data set was collected from AD patients in their naturalistic home environments (FIG. 5A). These data were used to evaluate the generalizability of the ML algorithm. A total of 10 participants (5 males and 5 females) participated in the training data collection, with ages between 22 and 27 years old (24±1.6). The validation data collection involved 11 patients (2 males and 9 females) with moderate to severe AD, with ages between 4 and 24 years old (10±9.1).

The training data were collected from healthy normal individuals. The participants performed a set of scratching and non-scratching activities, each lasting for approximately 35 s. The scratching activities were performed over clothes at the thigh, abdomen, upper arm, calf, knee, and shoulder. Each participant then scratched the skin at the inner elbow, outer elbow, forearm, dorsum of the hand, cheek, head, palm and neck. Rubbing was considered as a variation of scratching for purposes of these studies. These scratching activities were each performed twice, once while sitting on a chair and another while lying on a bed. For non-scratching activities, the participants waved their hands, sent text messages to friends, tossed and turned on a bed, sat idly, typed on a keyboard and tapped on a desk. These non-scratching activities were included as potential confounders for actual scratching activities. Data captured from each activity were saved as separate files with descriptions of each activity, annotated as scratching or non-scratching.

Figure 12:
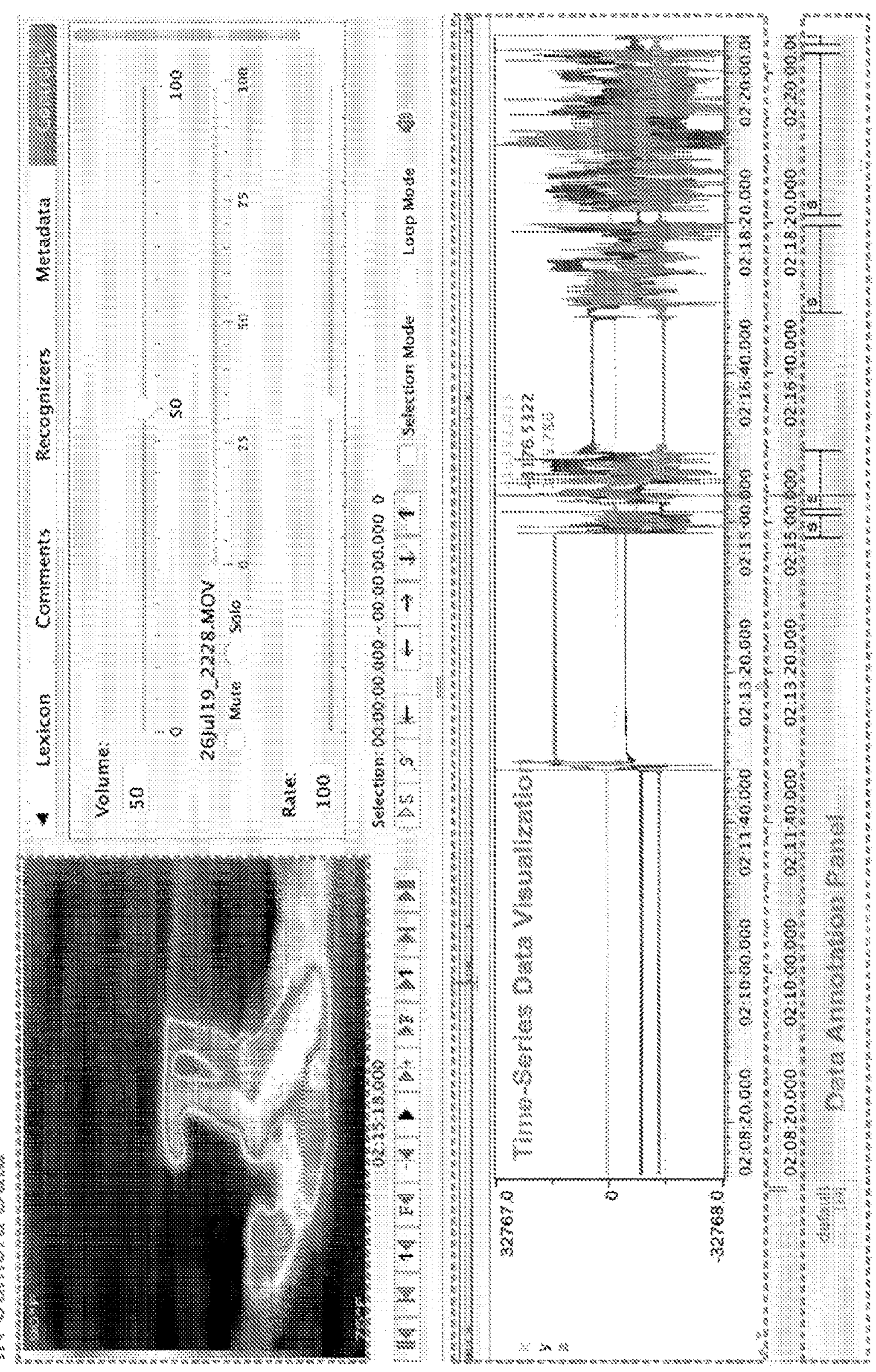
FIG. 12 shows time-series data collected from the ADAM sensor were synchronized with the IR video data on ELAN according to embodiments of the invention. The sensor data were annotated by visual assessment of patient's activities in natural home environment.

The validation data were collected from AD patients in their home environment as part of a clinical study approved by the Institutional Review Board of Northwestern University and the Ann & Robert H. Lurie Children's Hospital (IRB 2018-2111). The inclusion criteria included any patient with mild to severe AD older than 2 years of age. Patients with active skin or systemic infection were excluded. Eligible participants were screened in the Northwestern Medicine Department of Dermatology clinics and other pediatric dermatology or allergy providers at Ann & Robert H. Lurie Children's Hospital. A total of 11 subjects were recruited for the validation data collection (FIG. 5B). For subjects who agreed to participate, a written consent form was first obtained. Clinical research personnel then completed an eczema area and severity index (EASI) assessment and investigator's global assessment (IGA) of each patient. After completion of the EASI and IGA, each patient was trained on procedures for operating the ADAM sensor and collecting nocturnal data. During the training, the patients were provided with specific instructions about placing the ADAM sensor on the dorsum of the hand and securing it with a Coban self-adherent wrap. The patients then received a package containing the ADAM sensor, an iPhone, tripod, IR camera, charging equipment, instruction manual, and checklist. During the collection of validation data, each patient's nocturnal activities were recorded with an IR video camera. The ADAM sensor data was compared with the IR video data for data annotation. This annotation process was performed using a data visualization and annotation software (FIG. 12).

Sensor Operation and Performance

The ADAM sensor is a small, soft, stretchable wireless device that mounts using a thin adhesive onto the curvilinear surface of the dorsal hand, with an ability to be positioned across a range of possible anatomical locations and with various orientations (FIG. 1A). In certain embodiments, the ADAM sensor features a BLE radio, electronics and a rechargeable battery at one end of the sensor and at the other, a millimeter-scale, three-axis accelerometer with a sampling rate of 1,600 Hz at a resolution of 16 bits and a dynamic range of ±2g, where g is the gravitational acceleration, 9.8 $m/s^2$. Studies reported here focus on accelerations measured in a direction perpendicular to the surface of the skin. A thin, low modulus silicone elastomer forms a skin-compatible encapsulating package, as a watertight enclosure for a flexible printed circuit board (fPCB) that supports and interconnects these various components. The fPCB adopts a patterned layout that includes a collection of freely deformable, serpentine interconnects, specially designed by use of computational modeling to mechanically decouple the accelerometer from the other components of the device. This design optimizes the ability of the device to record subtle movements at the skin surface, accurately and without constraint. FIG. 1A presents images that highlight these "soft" mechanical attributes, and the overall "patch" form factor.

The high bandwidth 3-axis accelerometer in the ADAM sensor captures skin-conducted vibrations as well as overall motions associated with scratching behavior. The ADAM sensor captured acceleration along the x-axis and y-axis at a rate of 200 Hz, and the z-axis acceleration was sampled at a rate of 1,600 Hz. The x-axis and y-axis were oriented parallel to the skin surface whereas the z-axis was perpendicular to the skin surface. The high frequency content attenuates as the disturbance propagates from its point of origination at the fingertips, along the fingers and to the hand and, ultimately, the wrist. The location of the ADAM sensor determines, in this manner, the nature and quality of the signals. Experiments to examine the dependence on mounting location involved a set of scratching activities (10 s of scratching by articulating the arm and 10 s of finger scratching were performed, each separated by 5 s of idle state) repeated with different placements and orientations of the sensor. Based on signal quality and considerations in wearability, the ideal location is between the metacarpal $1^{st}$ and $2^{nd}$ digit.

Figures 6A, 6B:
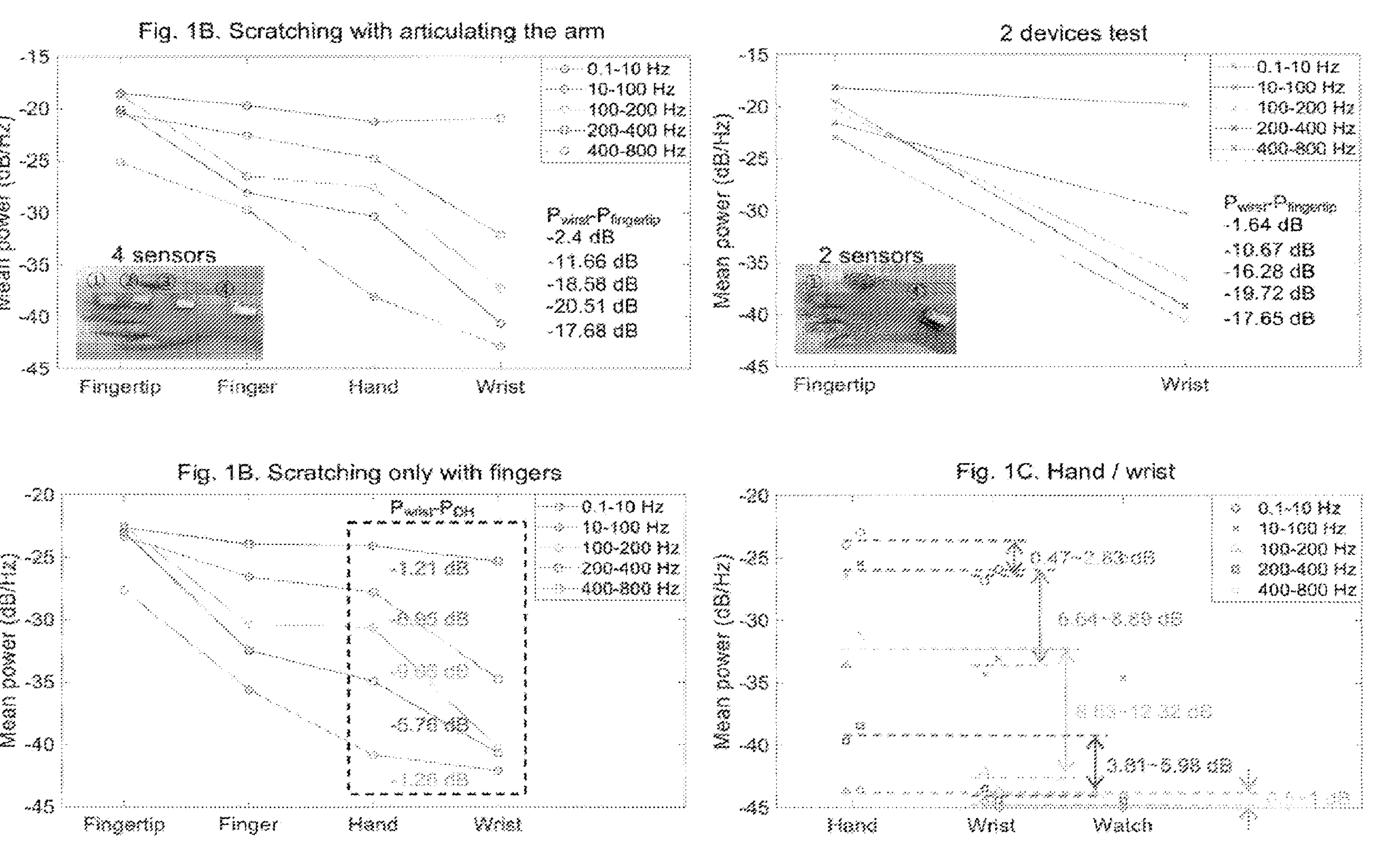
FIGS. 6A-6C show power dissipation according to embodiments of the invention.
Figure 6C:
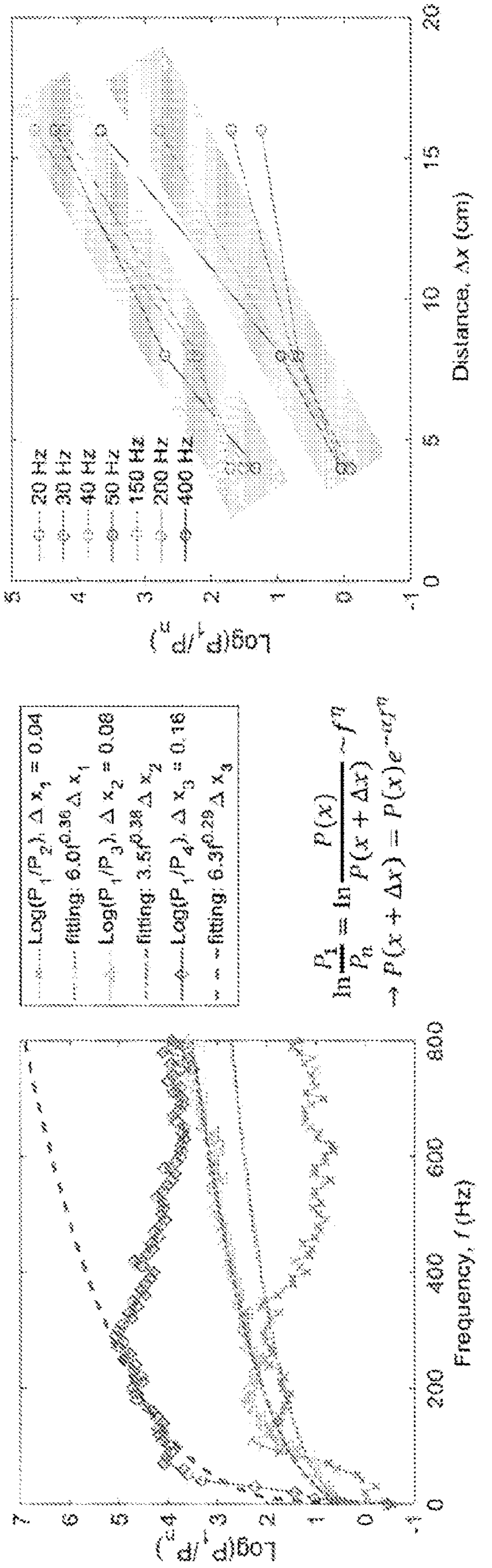

Scratching activities generate two types of signals. The first type of signals corresponds to gross movements of the hand, for which characteristic frequencies are in the range of a few Hz or less. The second type of signals, overlapping in time with the first type of signals, arises from subtle vibratory impulses generated by motions of the fingertips and fingernails against a contacting surface. Here, frequencies extend into the range of a few hundred Hz and exhibit amplitudes that decay rapidly with position along the fingers and into the hand, where they eventually pass through the wrist and to the arm. Detailed multi-accelerometer measurements hint at the physics of this second type of signals, although in the context of haptic interfaces. Similar direct measurements of accelerations at different locations from the fingertip to the wrist reveal the spectral characteristics of signal attenuation for the scratching behaviors, as shown in FIG. 1B. Measurements involve wireless accelerometers located at the fingertip, the midpoint along the finger, the dorsum of the hand, and the wrist, as in the right frame shown in FIG. 1B (also shown in FIG. 6A). The tests capture signals due to scratching the surface of the skin by articulating the arm for 10 s and then scratching with only the finger for 10 s. The peak to peak amplitudes of accelerations at the surface of the skin decay with increasing distance along the finger and the surface of the hand to the wrist. The color bars in spatial patterns in FIG. 1B represent the mean power of the signal per frequency in each frequency band. The left and right numbers indicate the maximum and minimum values for each of the respective plots. For scratching by articulating the arm (the first row of the spatial pattern), the power decays from 20 dB/Hz at the fingertips, the point of initiation, to −32 dB/Hz at the wrist in the frequency range from 10 to 100 Hz. The attenuation increases sharply with frequency. Specifically, the signal decreases from −19 dB/Hz to −37 dB/Hz and −20 dB/Hz to −41 dB/Hz for frequency ranges of 100~200 Hz and 200~400 Hz, respectively. For both types of scratching, the approximate power dissipation from the fingertip to the wrist is 2 dB in the frequency range from 0.1 to 10 Hz, 12 dB in the range from 10 to 100 Hz, 20 dB in the range from 100 to 200 Hz and 200 to 400 Hz, and 16 dB in the range from 400 to 800 Hz. As expected, the attenuation at low frequencies is much lower than that at high frequencies. The power of the signal decreases exponentially with increasing propagation distance and with increasing frequency. Power law frequency and distance dependent acoustic attenuation satisfies with $$P(x+\Delta x) = P(x)\exp(-\alpha_0 f^{\eta} \Delta x),$$

where P is the signal power, f is the frequency, Δx is the wave propagation distance, $\alpha_0$ is the attenuation coefficient, and q is a decay constant that is a frequency dependent characteristic of viscoelastic material obtained by fitting the experimental data. In the experiment in FIG. 1B, η has a value of 0.38 for the case of vibrations that propagate from the fingertip to the dorsum of the hand (FIG. 6C). These results suggest that critically important high frequency information associated with scratching can be captured most effectively by (1) locating the ADAM sensor in close proximity to the fingertips and (2) operating the accelerometer in a high bandwidth mode.

Figures 1C, 1D:
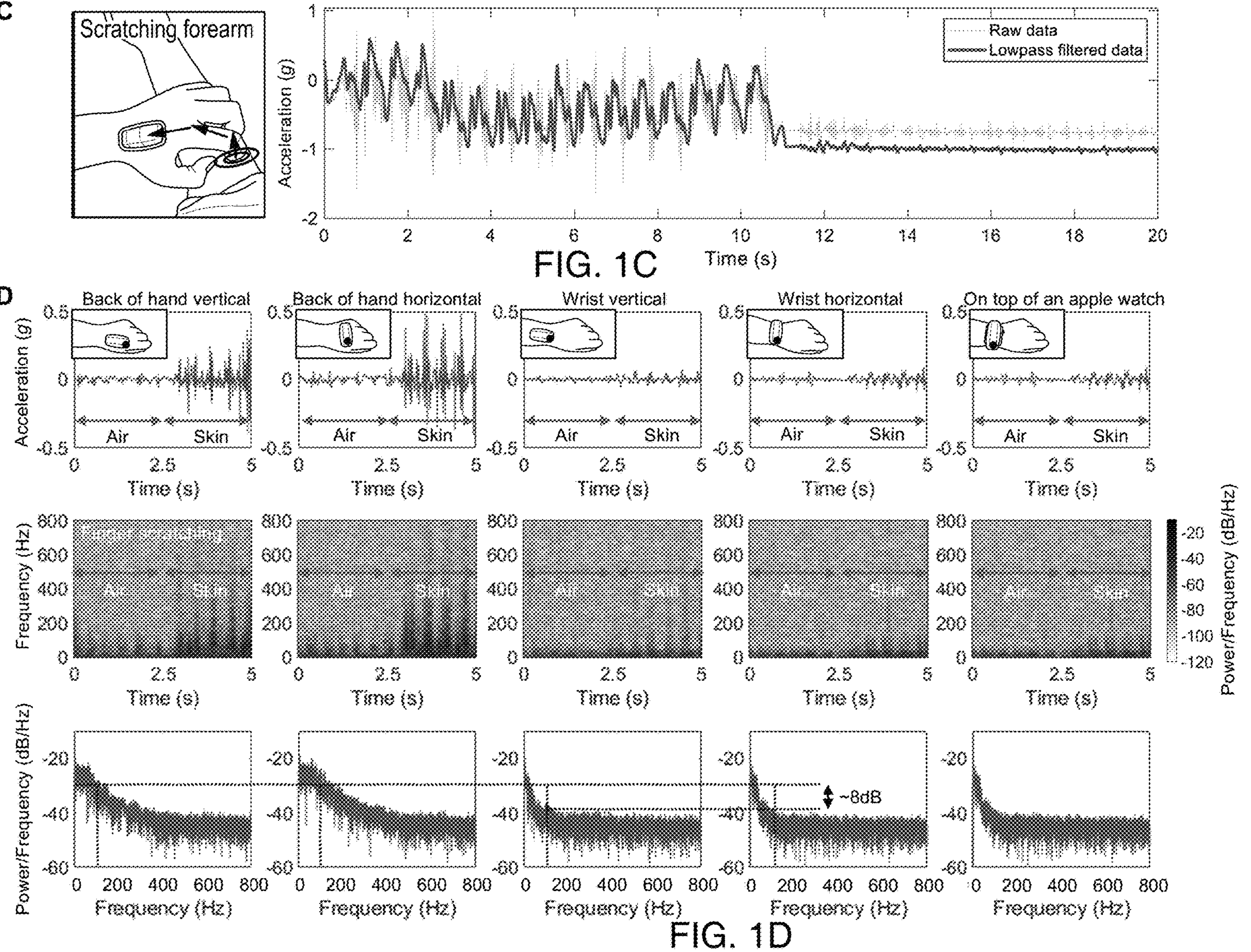

Existing scratch sensors use relatively low bandwidth accelerometers (typically 50 Hz or less) and associated electronics in rigid enclosures that couple to the wrist using bands. Although these existing devices can capture the first type of signals, they cannot record the second type of signals with adequate fidelity, consistent with the results of the propagation studies described above. This limitation follows from (1) a non-ideal mounting location, at the wrist, where high frequency signals have small amplitudes, (2) measurement bandwidths that are insufficient to capture high frequency information and (3) a loose mechanical coupling to the skin. The ADAM sensor, by contrast, quantifies both types of signals with high precision due to its proximity to the fingertips/fingernails, its high bandwidth operation and its intimate mechanical interface to the skin. The result is a superior capability for identifying scratching events with high specificity and sensitivity. FIG. 1C presents representative data generated by scratching the arm with the pointer finger of the opposing hand, as illustrated in the left frame. The motions involve (1) translating the hand, wrist and arm with the finger in a fixed position for 10 s and then (2) articulating the fingers only for 10 s. The two types of signals discussed above can be identified by passing the data through low pass and high pass filters with cutoffs at 2 Hz. The first type of signals represents the movement of the hand and can serve as the basis for detecting scratch events, but when used in isolation, without the second type of signals, can produce false-positive results from hand waving, essential tremor and other sources of motions unrelated to scratching. The critical high-frequency information originates at the fingertips and transmits through the soft tissue and metatarsal bones to the location of the sensor, as described above and illustrated by red arrows in FIG. 1C. These features, which are time synchronized with sliding of the fingertips and, in some cases, with motions of the hand, include energy across a broad range of frequencies. Although transmission through the body leads to attenuation that increases with frequency, particularly above 100 Hz, the associated complex waveforms are well preserved at distances of several centimeters.

Figure 7:
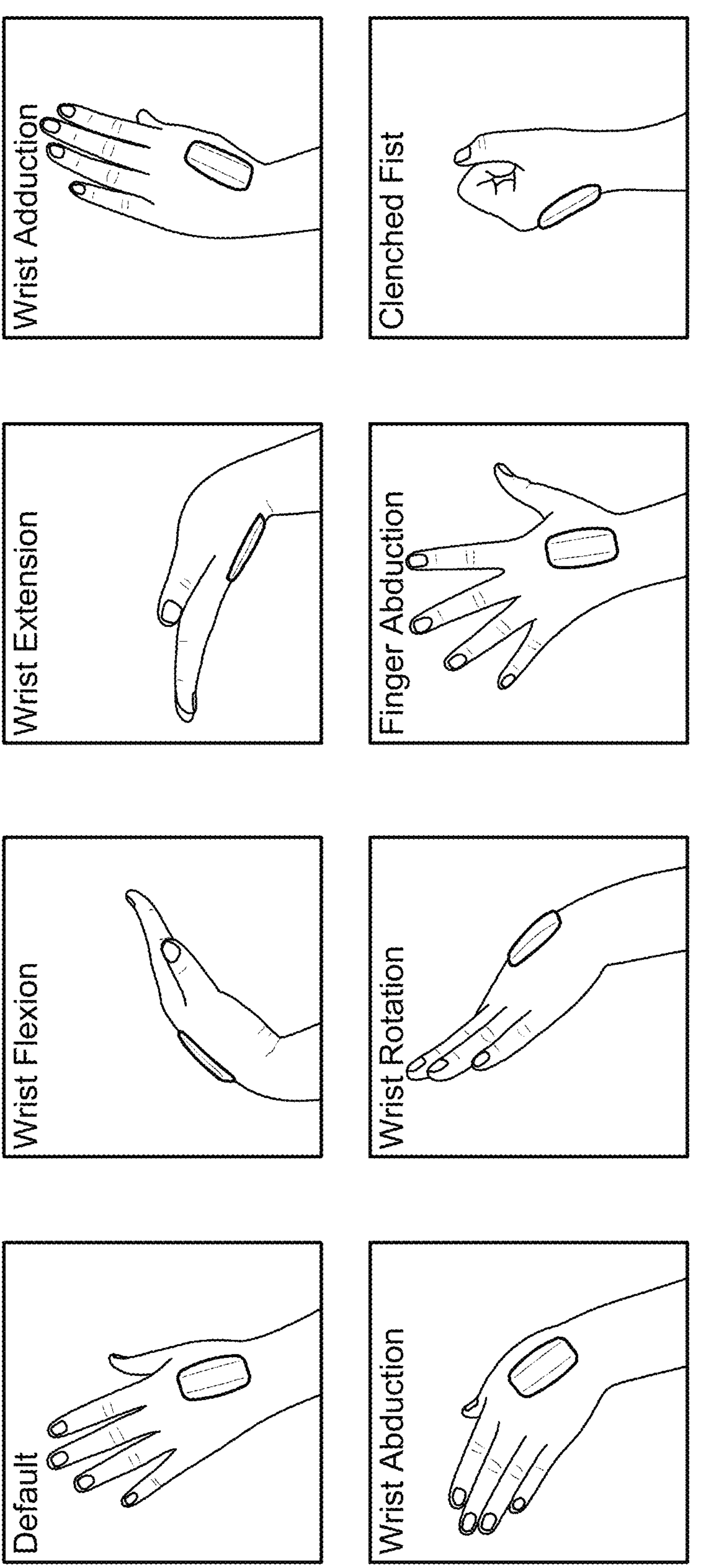
FIG. 7 shows the mechanical features allow the ADAM sensor to conform to the dorsum of the hand with various hand motions according to embodiments of the invention.

The effects appear in characteristics of signals captured by the ADAM sensor placed at the dorsum of the hand and the wrist with horizontal and vertical orientations, and on the top of a smartwatch (e.g., Apple Watch Series 4) tightly strapped to the wrist. Measurements involve first articulating the fingers with a scratching motion in the air for 2.5 s and then scratching the surface of the skin with the same motions for 2.5 s. Time series and spectrogram representations of the data in FIG. 1D clearly show the high frequency content associated with scratching the skin vs the air, in all cases. The spectrograms in FIG. 1D use a Hamming window with a frame size of 0.2 s and an overlapping duration of 0.19 s. These identifying features extend in frequency up to ~600 Hz, with some energy even up to 800 Hz, but with the most significant amplitudes in the range of up to 200 Hz. The results show only modest dependence on mounting location provided that the sensor is on the radial half of the dorsum of the hand. Orientation has little effect, simply because the accelerometer resides at the front of the ADAM sensor, as described previously and highlighted with a red dot in FIG. 1D. On the wrist, the high frequency components appear only as weak features in the data, consistent with the previous attenuation results shown in FIG. 1B (FIG. 6B). As mounted on the back of the hand where the signal strength is high, the soft physical properties of the ADAM sensor and the medical-grade, hypoallergenic single-use adhesive support a robust yet comfortable and non-irritating interface compatible with many daily activities involving various hand and wrist motions, as shown in FIG. 7.

Characterizing Scratching

Figure 13:
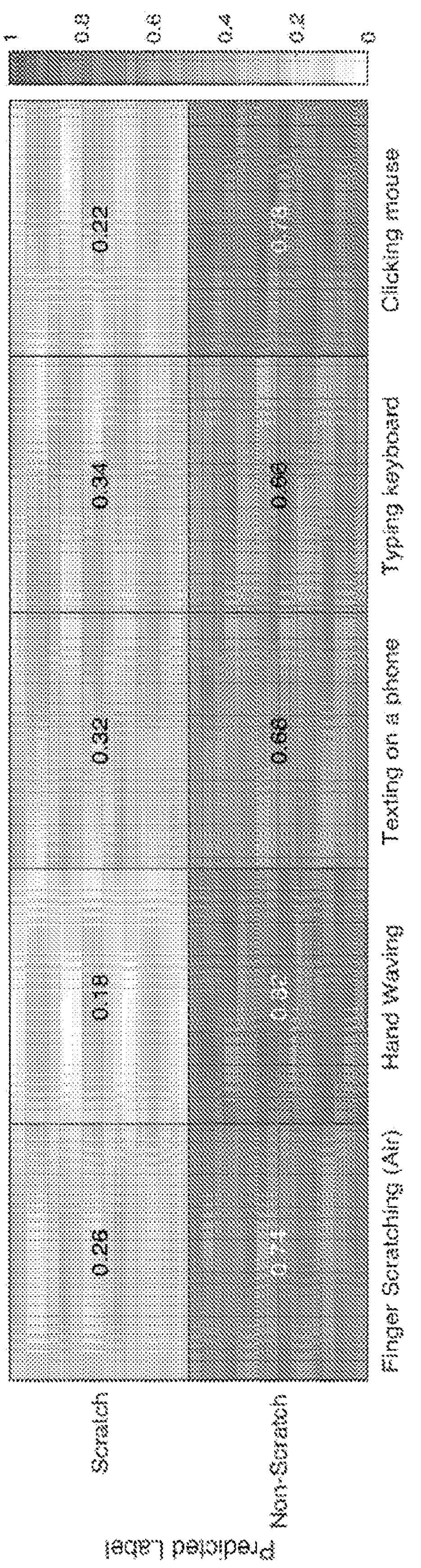
FIG. 13 shows probability of confounding non-scratching activities according to embodiments of the invention. The predicted probability for each class (scratch or nonscratch) was computed from the five confounding activities examined in this study. While scratching in the air, hand waving, and clicking a mouse were strongly predicted as non-scratching activities, typing on a keyboard and texting on a phone produced greater probability of scratching misclassification.

Scratching activity refers to a collection of movements that involve pressing the fingertips against a surface and moving the fingertips, causing friction. The friction between the fingertips and the surface generates vibrations that propagate along the surface. Scratching signals can differ from one another as the vibrations between the fingertips and the surface depend on many factors including but not limited to scratching speed, scratching intensity, and mode of scratching (e.g., only using fingers or moving the entire arm). Experiments to explore the time and frequency characteristics associated with these factors included scratching the head, arm, knee and leg and various non-scratching events such as hand waving, texting messaging, typing on a keyboard, clicking a computer mouse, and moving fingers in the air. FIG. 13 shows the predicted labeling for these confounders. The system performs best (>0.7) in distinguishing finger scratching in the air, hand waving, and clicking a mouse.

Scratching varies with individual, in response to both internal and external stimuli. Scratching can occur via articulation of the elbow, wrist, or fingers alone, as examined in the tests summarized above and shown in FIGS. 1B-1D. In the mode that engages the entire upper arm, the fingers press against the surface and remain stationary, where movement of the forearm articulating at the elbow joint drives the scratching action. The finger scratching mode, on the other hand, involves mainly local movements of the fingers, without significant forearm or wrist motion. Mixtures of these two modes are also possible. Depending on the location of scratching and the degree of itch, individuals interchangeably use different modes of scratching. For any type of scratching actions, the intensity is also important. The force at the point of contact determines the friction between the fingertips and the surface, and can therefore be considered, along with frequency and speed, as a metric of the intensity of a scratching event. These factors contribute to differences in signals captured by the ADAM sensor. Systematic studies for various types of scratching activities are important precursors to the development of a generalizable scratch detection algorithm.

Figures 2A, 2B:
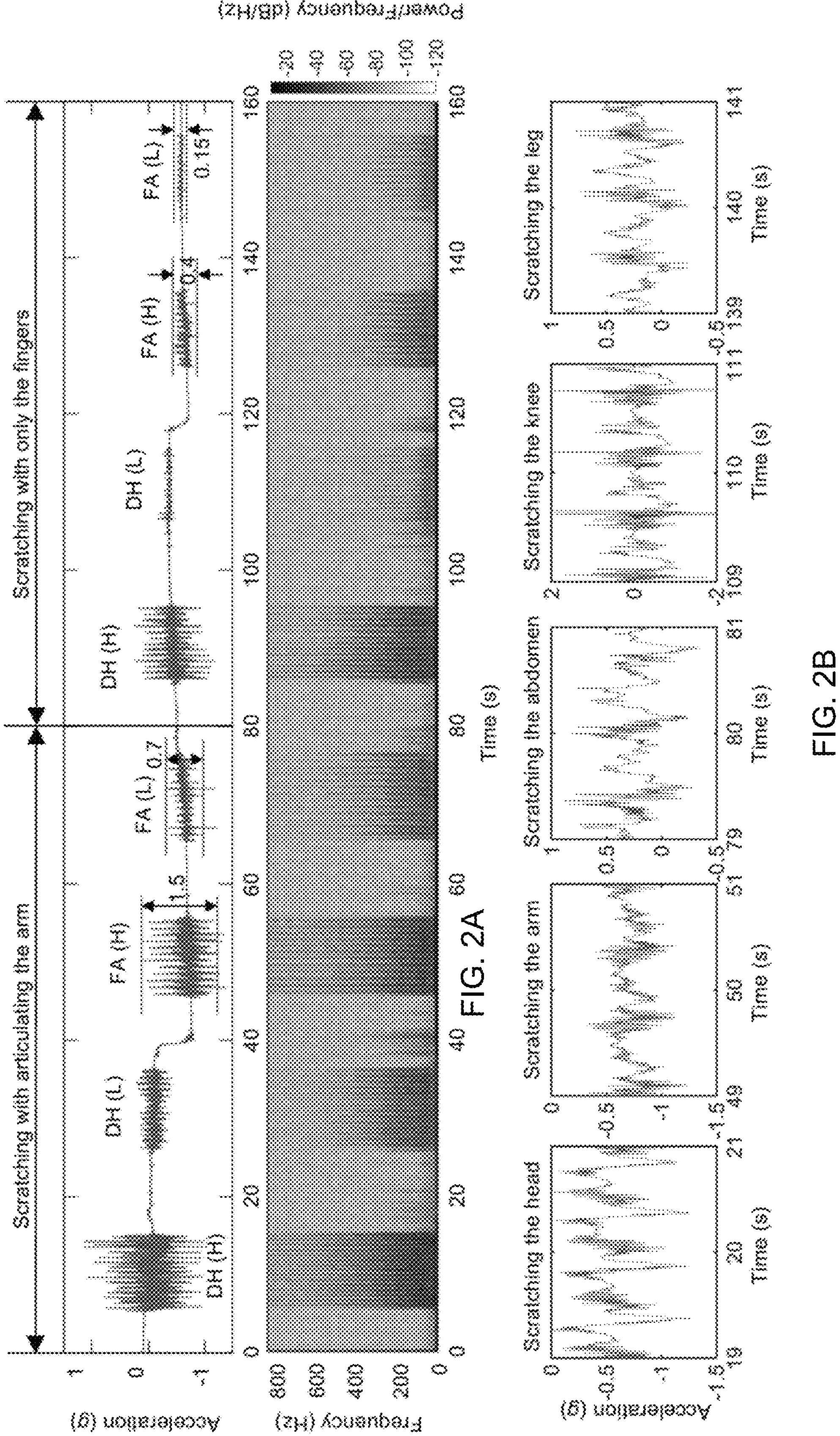
FIGS. 2A-2E show representative data collected by the ADAM sensor according to embodiments of the invention.
Figures 8A, 8B:
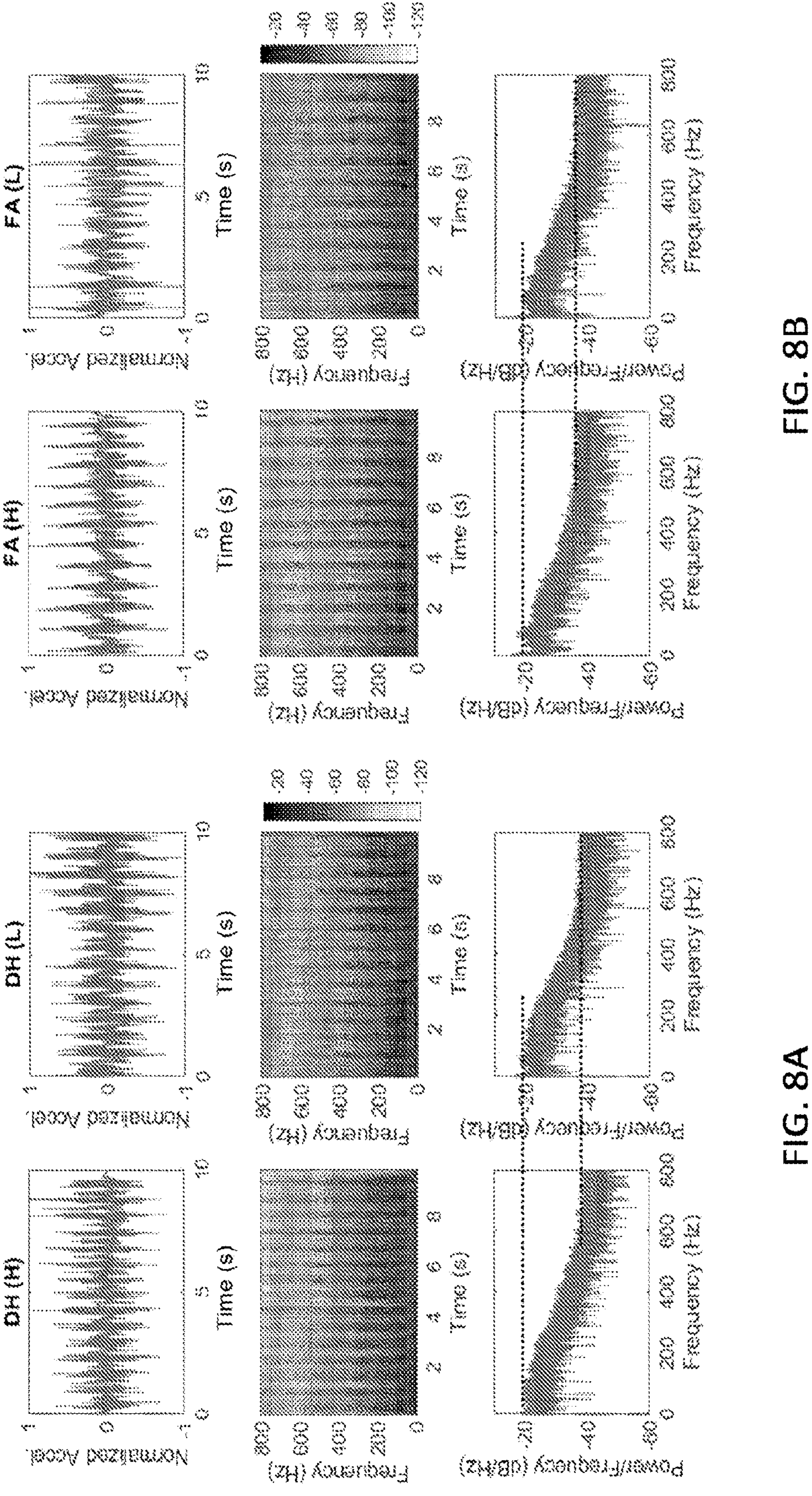
FIGS. 8A-8D show the normalized time series and spectral characteristics of two modes of scratching (scratching with articulating the arm and scratching only the fingers) and two body parts (dorsal of the hand and forearm) according to embodiments of the invention. The spectral characteristics of high intensity and low intensity scratching events are largely the same when the scratching mode and the scratching location are the same. Time series data plots, spectrograms, and Fourier transforms of scratching with high and low intensities.
Figures 8C, 8D:
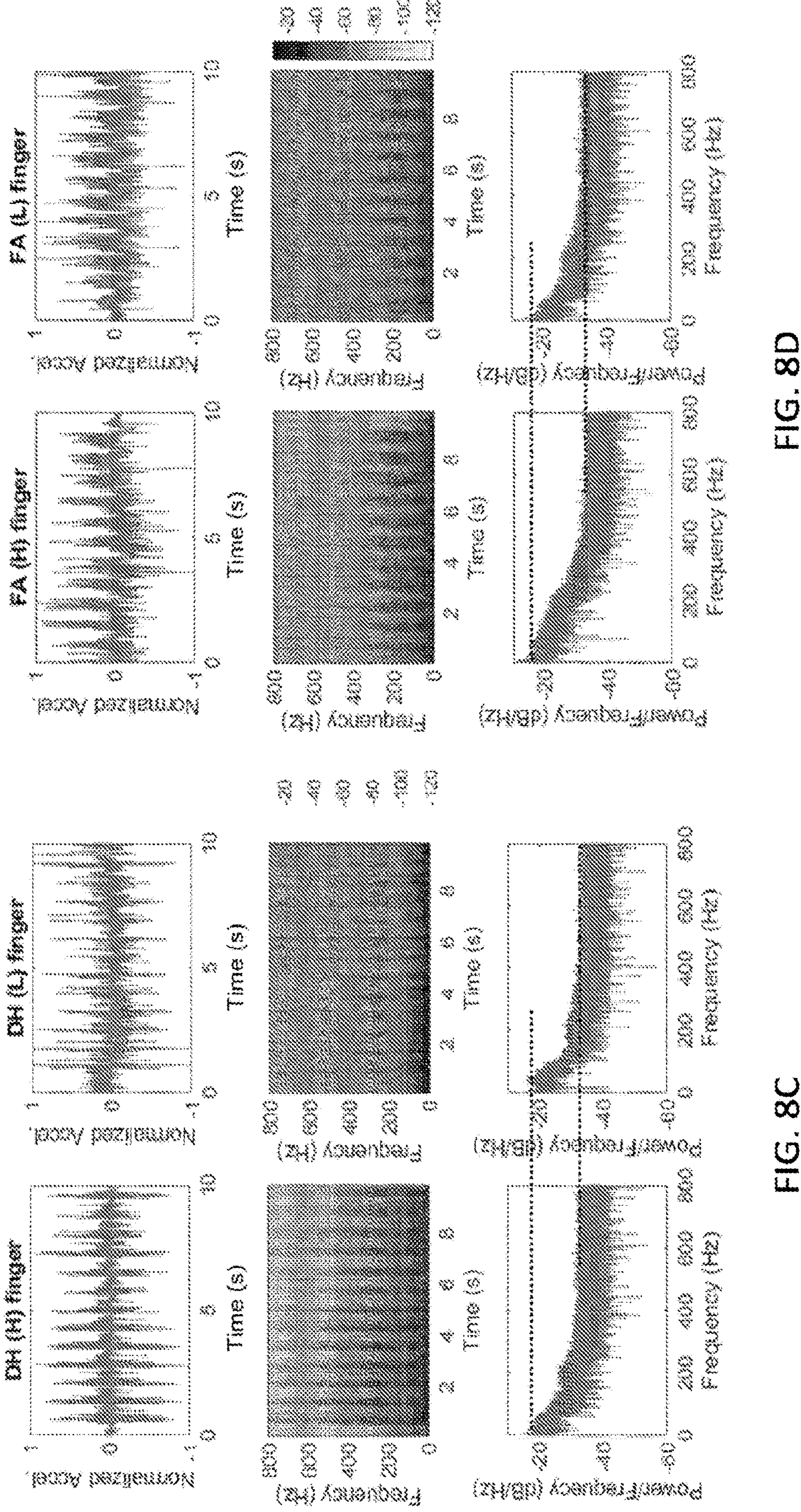
Figure 9:
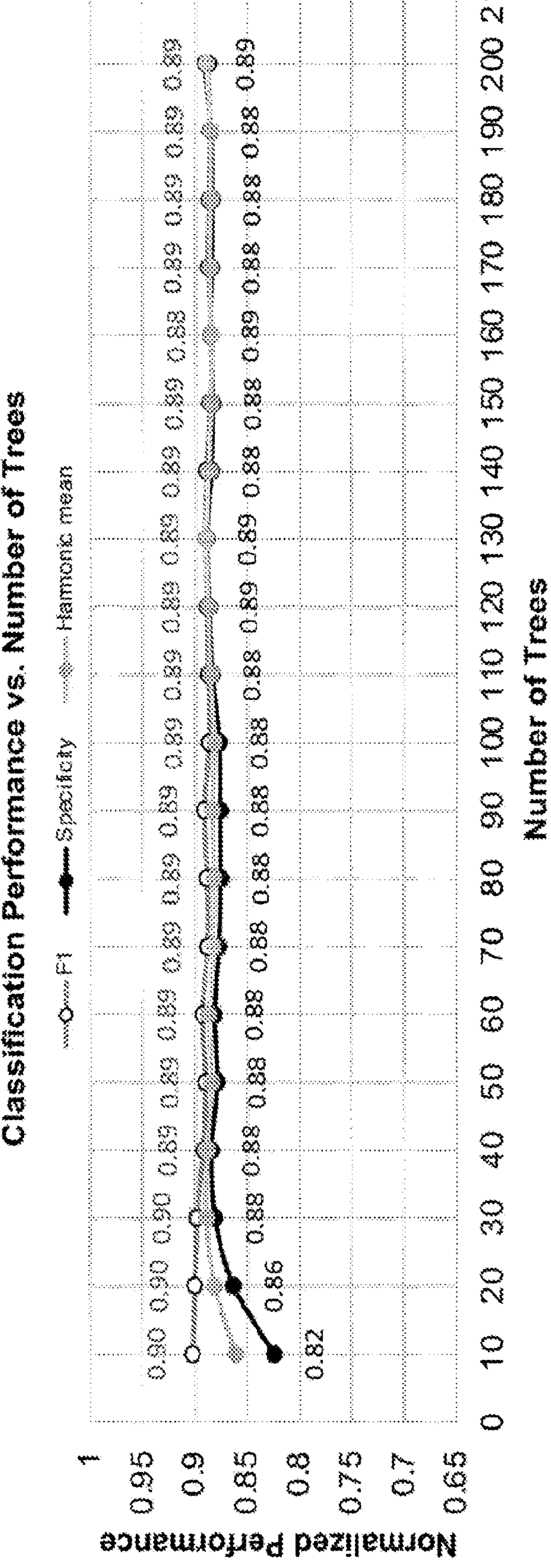
FIG. 9 shows effect of the number of trees on classification performance. Minimal benefits follow from use of more than 50 trees according to embodiments of the invention.

Control experiments for this purpose involve two body locations: dorsum of the hand (DH) and forearm (FA) (FIG. 2A), with the ADAM sensor on the left dorsal hand, as shown in FIG. 1D, with two locations scratched with the left hand by articulating the arm only and then the fingers only, at a high intensity followed by a low intensity. The blue solid line in FIG. 2A shows the time-dependent z-axis acceleration from the vibrational motions at the surface of the skin, in a direction orthogonal to the plane of the scratching motion. The peak-to-peak amplitudes are larger for high intensity scratching than for low intensity, as expected. For instance, the amplitude of the signal for high intensity FA scratching (45~55 s) is 1.5 g which is more than two times greater than that for the low intensity case (65~75 s; 0.7 g). For an otherwise similar scenario but by articulating only the fingers, the amplitudes of the high (125~135 s) and low (145~155 s) are 0.4 g and 0.15 g, respectively. Results for articulating the arm only (0~80 s) show amplitudes larger than those for the fingers (80~160 s) for each scratch location (HD, FA) and intensity level. The frequency domain content associated with these signals appears as spectrograms (FIG. 2A), plotted using same window and frame size as FIG. 1C. In all cases, even at low intensity with fingers only, the high frequency content, especially up to ~200 Hz, features prominently in the data. The normalized spectral characteristics of high intensity and low intensity scratching events are largely the same, as in FIG. 8.

Figures 2C, 2D, 2E:
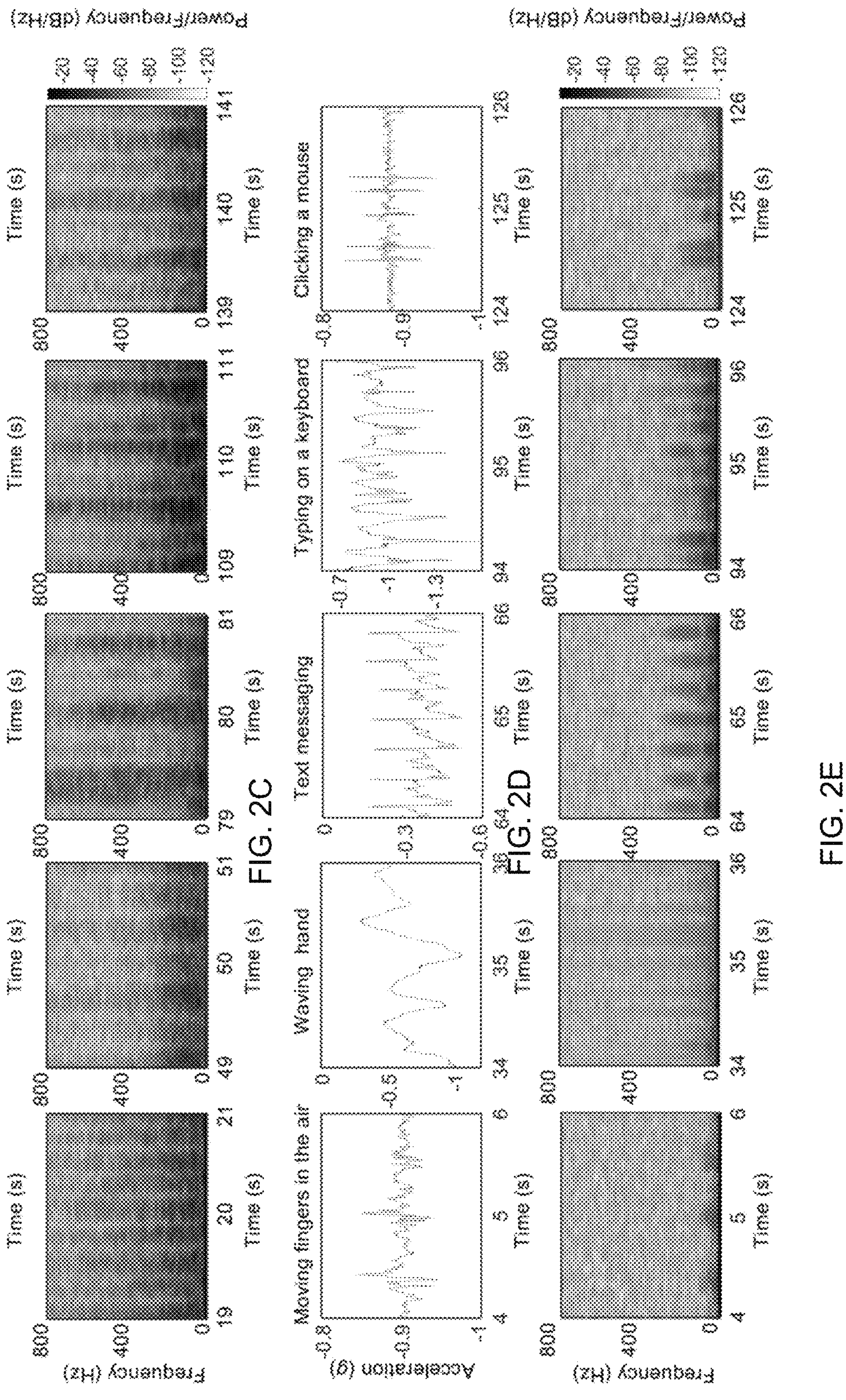

Scratching activities on five different body locations (head, arm, abdomen, knee, and leg) and non-scratching activities (simulating scratching with fingers in the air, hand waving, texting using a cell phone, typing on a keyboard, and clicking a mouse) highlight the key differences in the signals and the importance of the high frequency content in a range of practical scenarios (FIGS. 2B and 2D). Specifically, the data for all scratching activities have significant energy above 200 Hz, independent of location (FIG. 2C). As expected based on previous discussions, the spectrograms of most non-scratching activities exhibit minimal energy in this frequency range (FIG. 2E). Text messaging, typing on a keyboard, and clicking a computer mouse represent exceptions, where the data show contributions between 100 Hz and 200 Hz due to impulse components of these motions. Nevertheless, the spectral content across all frequencies, the temporal characteristics of the signals and the low frequency information can help to distinguish such activities from scratching. In other words, the high frequency components of the recorded signals are important indicators of scratch, but they must be used together with other features of the data to achieve high selectivity against a certain, relatively small, set of confounding activities. Furthermore, measurement of nocturnal scratching mitigates the need to differentiate from awake activities such as typing or text messaging. As an illustration, FIGS. 14-15 highlight a form of manual signal analysis that involves translation of the raw data into an audio file that can be interpreted in a manner analogous to that of sounds from a stethoscope. Various activities such as those described above can be immediately distinguished from scratching in this manner. These collective considerations motivate a machine learning approach to data analysis, in which various features, including but not limited to high frequency content, contribute to a classification scheme for unmatched combined levels of sensitivity and specificity.

Hand-Mounted vs Wrist-Mounted Scratch Sensing

As mentioned above, scratching behavior can occur via articulation of the fingers, wrist, elbow, or shoulder. A key limitation of wrist-mounted sensors is the inability to measure motion associated with finger-only scratching and in difficulties in distinguishing between hand waving and scratching. Control studies reveal the performance of the ADAM sensor compared to a wrist-bound system (e.g., Apple Watch Series 4) with an embedded mobile application to quantify scratch.

Figures 3A, 3B:
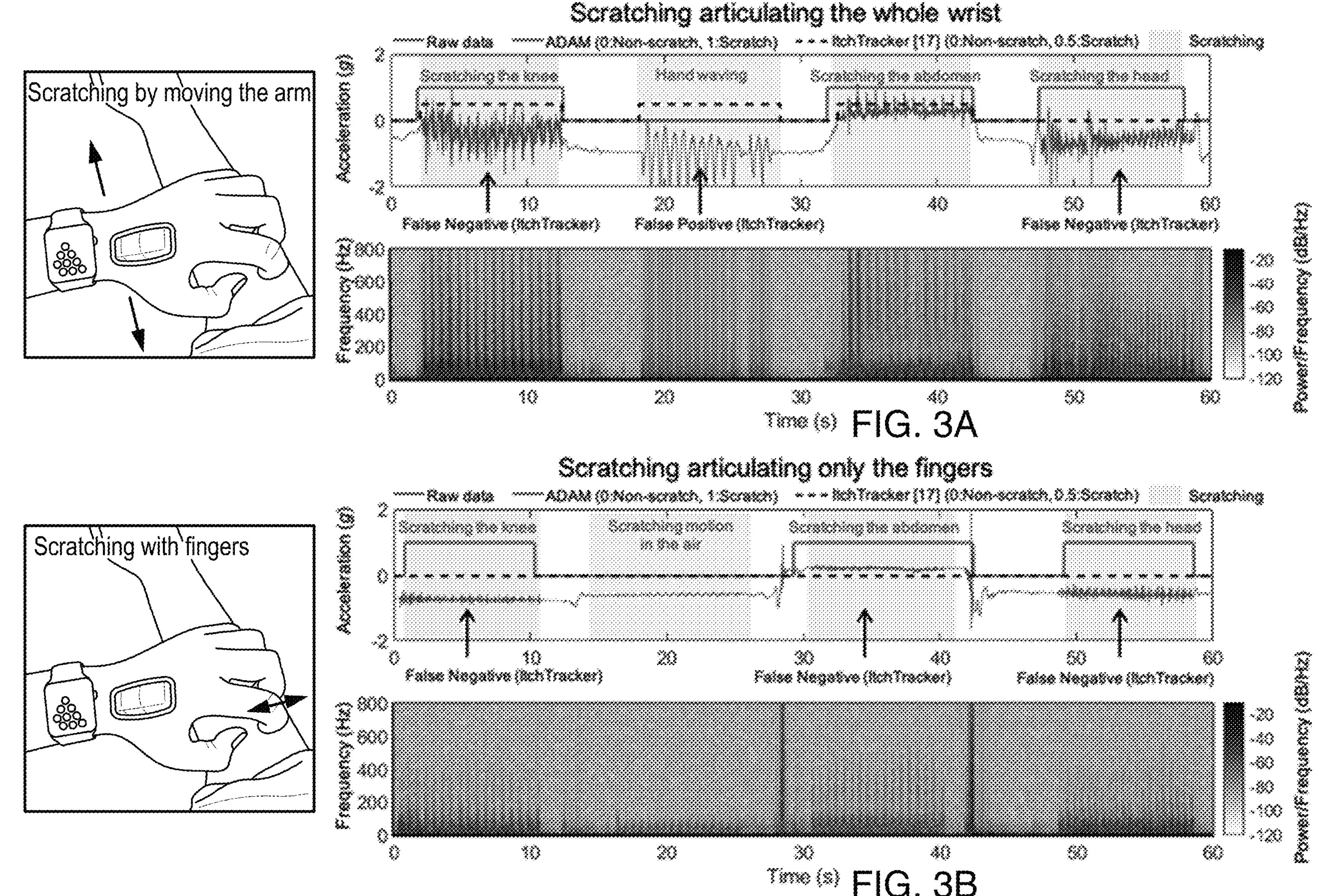
FIGS. 3A-3B show comparison of results obtained with an ADAM device on the hand and an AppleWatch with the ItchTracker Mobile Application, according to embodiments of the invention. Time series data and the spectrograms for various scratch (skin over the knee where there is a bony prominence, skin of the soft abdomen, the skin of complex surface head) and non-scratch activities (waving hand, scratching motion in the air), with a 5 s pause between each activity.

As shown in the left frame of FIG. 3A, an AppleWatch Series 4 was placed on the left wrist, and an ADAM sensor was placed on the dorsum of the left hand. This configuration was intended to synchronize the data collected from both devices for purposes of direct comparisons. Tight coupling of the AppleWatch Series 4 to the dorsum of the left hand was verified by ensuring that the smartwatch could not be rotated freely around the wrist. Similarly, the tight attachment of the ADAM sensor was verified by flexing and extending the left hand, ensuring the ADAM sensor stayed in contact with the skin. After placing the sensors, a set of scratching and non-scratching activities were performed in sequence shown in the left frames of FIGS. 3A-3B. One of the scratching activities involved the movement of the entire arm/hand, while the other scratching method only used fingers. Additionally, simply hand waving activity was performed to determine an ability to differentiate simple hand motion from scratching activity.

The comparison focuses on two modes of scratching: one by articulating the arm and the other by only the fingers. To examine scratching by articulating the arm, the set of activities include knee scratching, hand waving, abdomen scratching, and head scratching in a sequence for 10 seconds separated by 5 seconds of pause, as shown in FIG. 3A, where the blue line represents the time series of the raw data, and the red line indicates the final binary classification results where 0 and 1 correspond to non-scratch and scratch, respectively. The black dashed line in FIG. 3A highlights the classification results from an App, ItchTracker, with 0 representing non-scratch and 0.5 scratch activity. While the ItchTracker captures knee scratching and abdomen scratching, it misclassifies hand waving and head scratching. The former likely follows from a heavy reliance on hand motions for scratch detection. The latter probably occurs because head scratching involves only short range of motions of the wrist. The ADAM sensor performs well across all of these and other scenarios.

Additional experiments explore scratching modes that involve only finger articulation (FIG. 3B). As with the previous comparison using the arm for scratching, the four activities include knee scratching, simulating scratching in the air, abdomen scratching, and head scratching. In these activities, the ItchTracker does not detect any instances of scratching due to the lack of motion at the wrist. On the other hand, the ADAM sensor detects all instances and it even accurately discriminates scratching from pseudo-scratching (FIG. 3B). Simulated scratching motion in the air provides an additional test of the ADAM system. The major difference between scratching and pseudo-scratching is the presence of frequency signatures above 100 Hz. While the ADAM system can capture frequencies as high as 800 Hz, most wrist bound accelerometers such as the Apple Watch record frequencies only as high as 50 Hz (i.e. sampling rate of 100 Hz).

Data Analysis and Validation

Figures 4A, 4B:
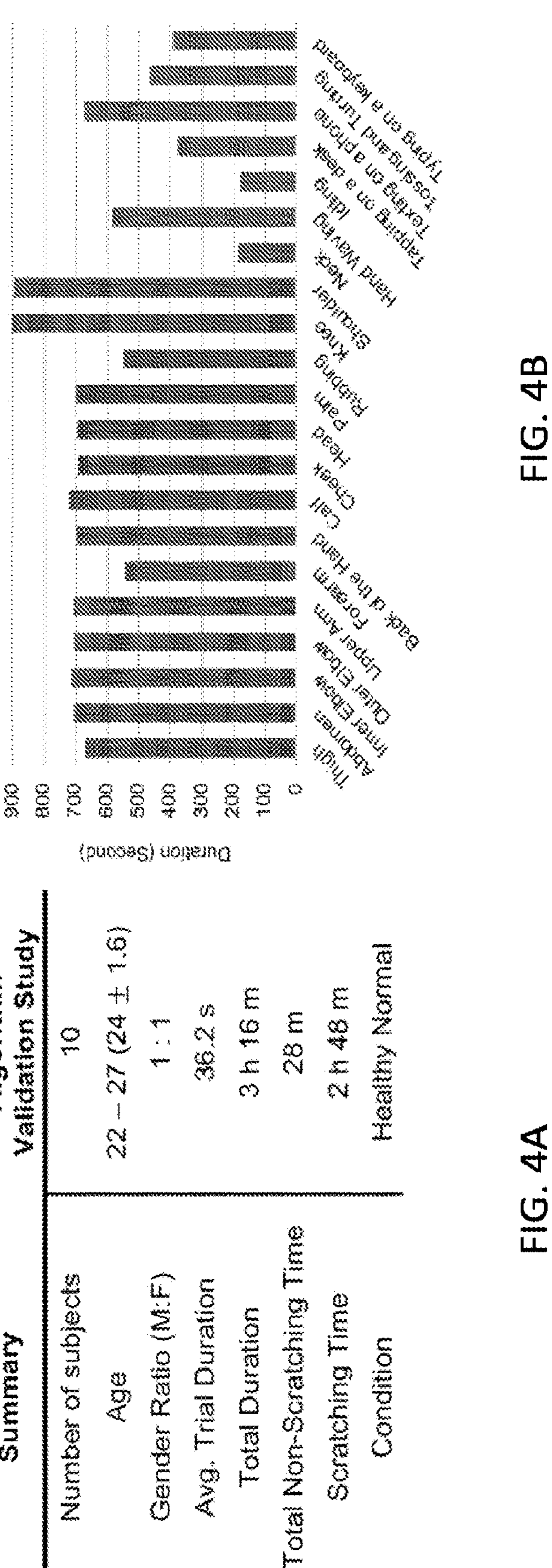
FIGS. 4A-4E shows overview of data sets, signal processing pipelines, and validation methods, according to embodiments of the invention.
Figure 4C:
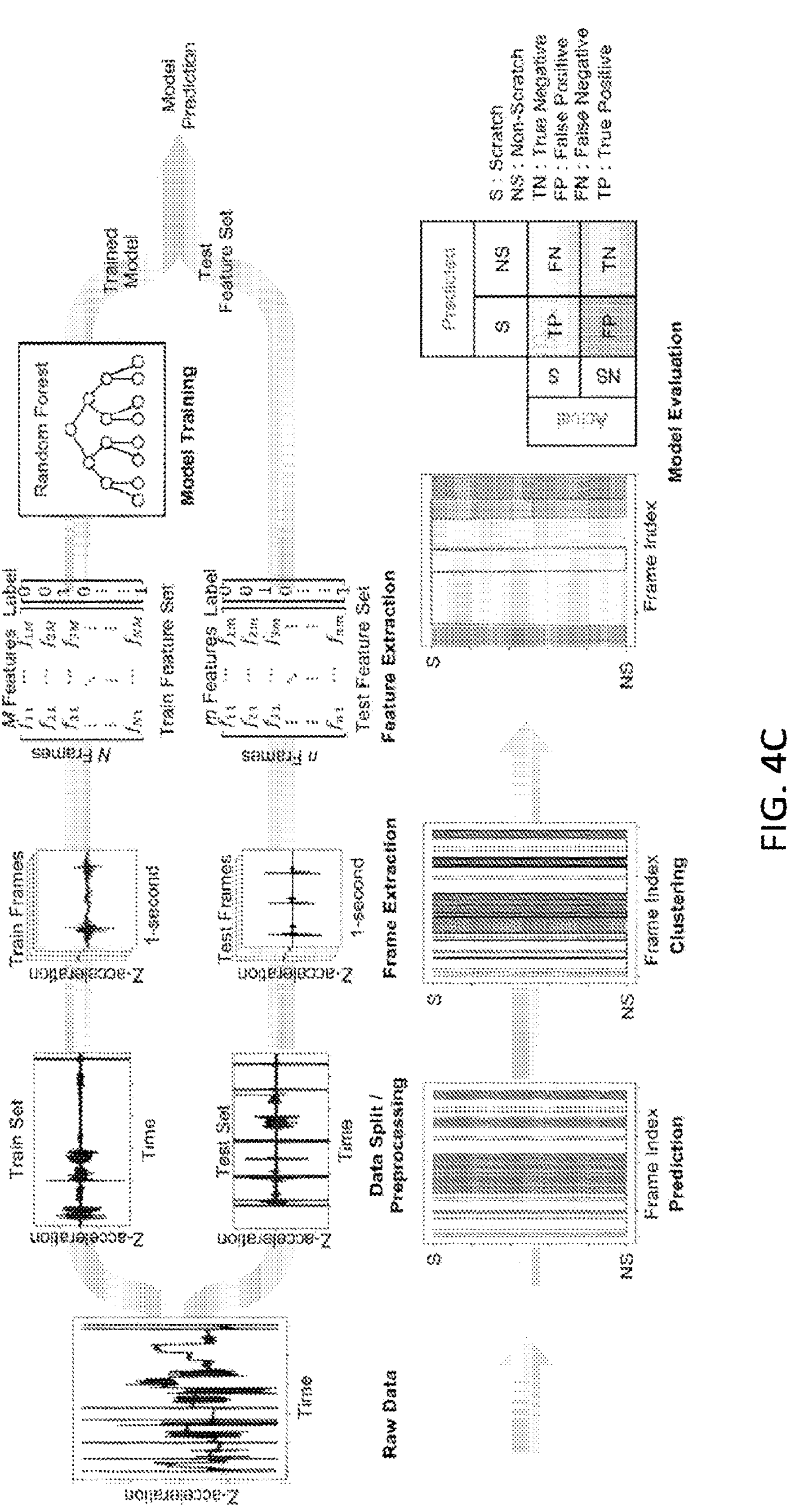

In this exemplary study, we focused on the z-axis acceleration data because the critical information about scratching pertains mainly to out-of-plane skin vibrations. The raw z-axis acceleration data was processed through a signal processing pipeline as illustrated in FIG. 4C. In the first step, the raw data was passed to the preprocessing block to remove the baseline wander of the data caused by slow, large-scale motions. Thus, low frequency baseline wandering is removed from the signal processing pipeline to allow for greater emphasis of the more specific high frequency signal components. Subsequently, the preprocessed z-axis acceleration data were segmented into frames by sliding a 1-second window with an overlap. For training, 90% overlap was used and for testing 50% overlap was used. Each frame was assigned a label of 0, indicating non-scratching activity, if less than 50% of the data points in a given frame were labeled as scratching activity. Otherwise, the frame was assigned a label of 1, indicating scratching activity. From each frame, a set of features shown in FIG. 5C were extracted, and these features were used to train and validate a random forest (RF) classifier.

Both the random forest (RF) classifier and the leave-one-subject-out cross validation (LOSO-CV) are used in the exemplary study for algorithm validation. Cross validation (CV) has been frequently employed in many machine learning applications as it provides a simple and effective way of evaluating classification models. In the CV, the number of folds is a parameter that specifies how data is split into training and testing sets. The LOSO-CV is used to assess the performance of the model as it is known to perform well on real world data. After the model was optimized on the training data set, we evaluated the performance of the model in cross-study validation where the trained model is applied to the clinical validation data set collected in natural. The cross-study validation examines the generalizability of the algorithm as the training data set and the validation data sets were independently collected.

The RF classifier allows automated detection of scratching activities. The training data set contains scratching data from 15 different body locations and 6 types of non-scratching activities collected from 10 healthy normal subjects, as shown in FIGS. 4A-4B. Results from the LOSO-CV applied to the training data set form the basis for optimization of the RF classifier. In this process, a data set from a single participant serves as the testing data set, and the remaining data allows for training. Iterating this process across all participants allows each participant's data to be used for testing once. The classification performance corresponds to averages from all iterations of the validation. The LOSO-CV, unlike k-fold CV approaches, prevents the classifier from learning a confounding relationship within a subject's data set with unrealistically high classification accuracy.

The RF model can be optimized by comparing the LOSO-CV outcomes. The parameters for this optimization include the number of trees in the RF classifier and the minimum required scratching duration.

The RF classifier is a meta estimator that fits a number of decision tree classifiers on various sub-samples of a data set. The choice of number of trees in the forest fairly balances the complexity of the model and its performance. Increasing the number increases the training time, as well as the potential for overfitting. Thus, the optimization focuses on examining a different number of estimators, from 10 to 200 trees, and comparing the LOSO-CV performance. The classification performance reaches a maximum value at approximately 30 decision trees.

The minimum required scratching (MRS) duration represents another optimization parameter. In the signal processing pipeline, as shown in FIG. 4C, the RF classifier returns predictions at a 1-second frame level. The outputs are subsequently clustered using density-based spatial clustering of applications with noise (DBSCAN). The purpose of the DBSCAN is to join two scratching frames in close proximity as a single scratching event.

Figure 10:
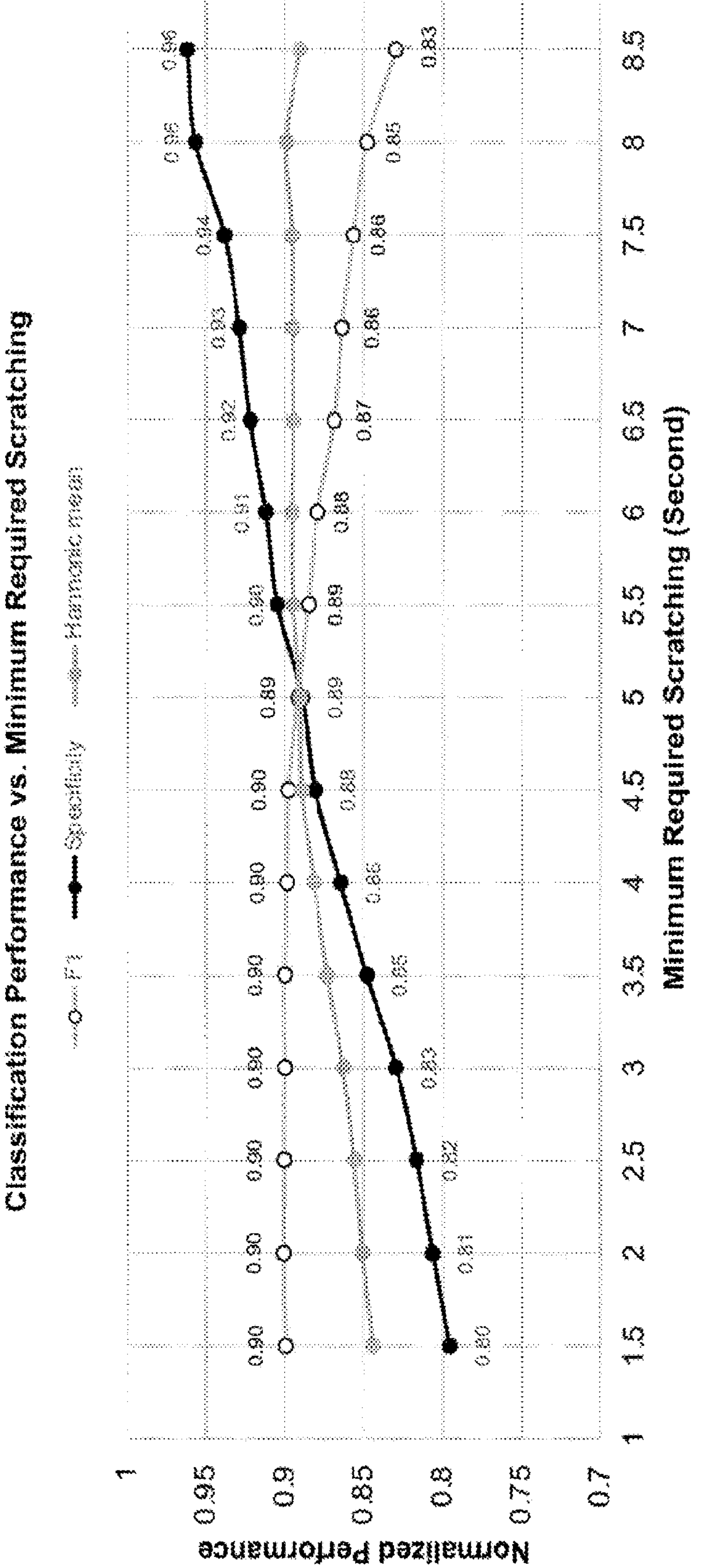
FIG. 10 shows effect of minimum scratching duration windows on the sensitivity and specificity of the definition of a scratching event according to embodiments of the invention. The best performance is achieved when the minimum required scratching is 4.5 seconds. As the minimum required scratching increases from 1.5 seconds to 8.5 seconds, the specificity increases and the F1-score decreases.

In the DBSCAN, two important parameters eps and min_samples that define the clustering rules need to be optimized. The parameter eps specifies the maximum step size that a cluster can take to decide whether or not a sample (in this study, a frame) belongs to the cluster. For instance, eps of 5 frames means that two frames that are apart from each other by 5 frames or less can be merged as a single cluster. In terms of temporal distance, this corresponds to 3 s with 1-second frame size and 50% frame overlap in sliding window analysis. The parameter min_samples determines the minimum required samples to form a cluster. For instance, min_samples of 5 frames means that a cluster contains greater than or equal to 5 samples (or 5 frames in this application). The implication of min_samples of 5 frames is that at least 5 consecutive scratching frames, which corresponds to 3 seconds given 50% overlap between frames, are required for the system to detect a sequence of frames as a scratching activity. To find the optimal values, eps and min_samples values were varied from 2 frames (1.5 s) to 16 frames (8.5 s) with an increment of 1 frame for both training and validation data sets, as shown in FIG. 10. The results suggest that an eps of 10 frames (5.5 s) and a min_samples of 8 frames (4.5 s) achieve the best performance. This implies that a minimum of 4.5 s of continuous scratching is required to form a scratching activity. The algorithm can detect two consecutive scratching frames, separated by less than 5.5 s of non-scratching activity, as a same cluster. In simple terms, one has to scratch for at least 4.5 s continuously for the algorithm to cluster the scratching as a scratching event, and the person is allowed to engage in a non-scratching activity up to 5.5 s without the algorithm separating the scratching from the previously identified scratching event, as shown in FIG. 10. As the min_samples was reduced from 8 frames (4.5 s) to 3 frames (1.5 s), the F1-score remained at 90% whereas specificity decreased to 80%, as shown in FIG. 10. This analysis demonstrates that there is a tradeoff between scratch sensitivity and specificity.

The MRS defines the minimum number of frames to form a cluster of scratching events, and is corresponding to the parameter min_samples. As shown in FIG. 10, the MRS values from 1.5 to 8.5 s yield different classification performance using the LOSO-CV. The performance increases with increasing the MRS duration up to 4.5 s and then remains constant for values up to 8.5 s. Improved performance can be achieved with further increases in MRS, but with diminishing returns. For the analysis below the MRS is defined as at least 4.5 s.

Figures 4D, 4E:
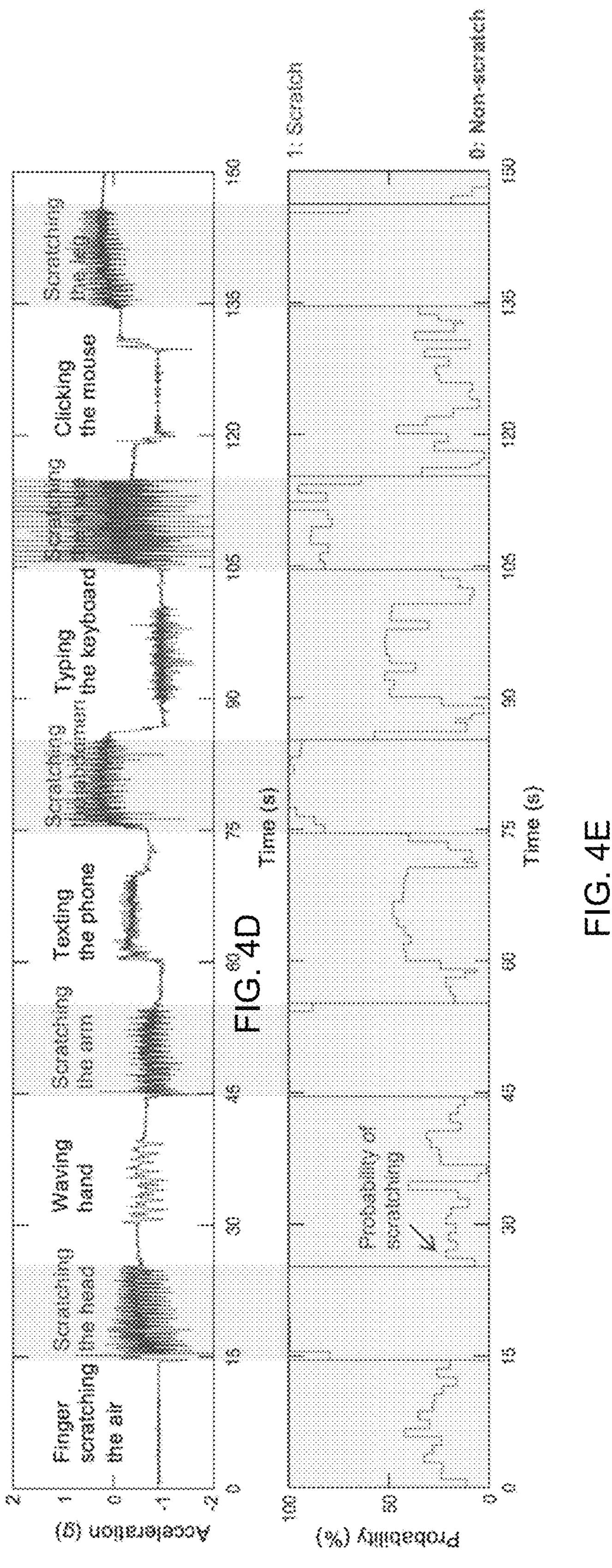

The optimized RF classifier is applied to data collected from a single subject performing various scratching (the head, the arm, the abdomen, the knee and the leg) and non-scratching activities (simulating scratching in the air, hand waving, texting on the phone, typing a keyboard, and clicking a mouse). The corresponding time series z-axis acceleration data are in FIG. 4D, and the associated classification results are in FIG. 4E.

With the optimized RF classifier (30 trees) and MRS duration (4.5 s), the LOSO-CV can be applied to the healthy, normal training data set to evaluate the performance. The results indicate an average precision is 94.4% and the average sensitivity is 87.8%. The overall accuracy is 89.1%. Table 1 summarizes the overall performance.

The RF classifier trained on the algorithm validation data set can be used directly on the patient data set from the clinical validation study. This evaluation reveals an average precision of 82.5%, an average sensitivity of 84.3%, and an overall accuracy of 99.0% with a sensitivity of 84.3% and specificity of 99.3%, as shown in Table 1. The clinical study included manually labeled datasets from all 46 nights with the ADAM sensor mounted on the dominant hand of each subject.

TABLE 1

Classification results.

| | Algorithm Validation Study (n = 10) | Clinical Study (n = 11) |
|---|---|---|
| Sensitivity | 87.8% | 84.3% |
| Specificity | 88.1% | 99.3% |
| Accuracy | 89.1% | 99.0% |
| Precision | 94.4% | 82.5% |
| F1 Score | 89.8% | 82.9% |

Figure 14:
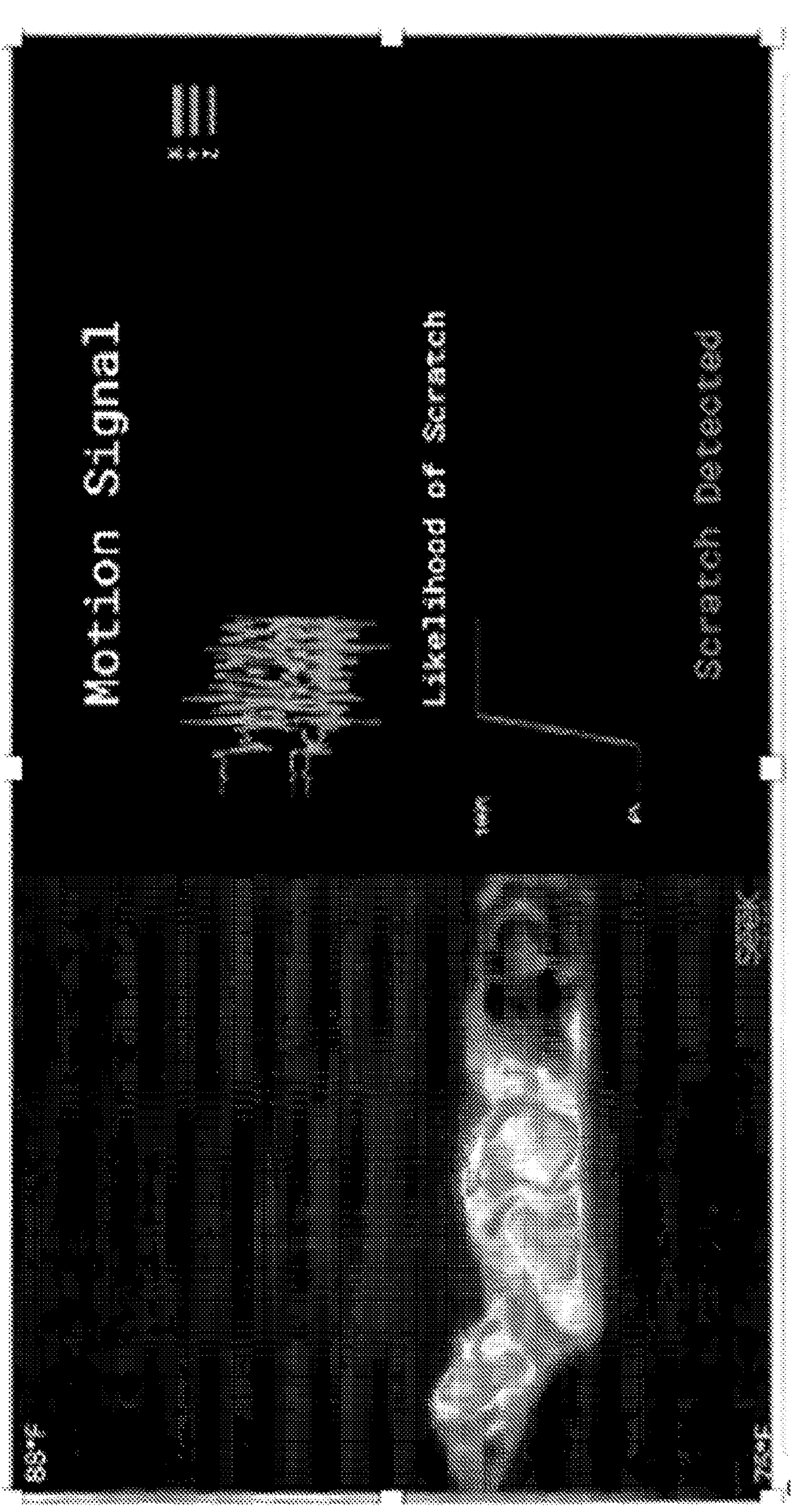
FIG. 14 is a screenshot of a video illustrating a pediatric patient with AD wearing the ADAM sensor while scratching. Pediatric patient with severe atopic dermatitis is wearing the ADAM sensor with concomitant video recording of scratching. Note that scratch intensity varies in the video. The algorithm correctly identifies scratching intensity through the amplitude of the sensor response.
Figure 15:
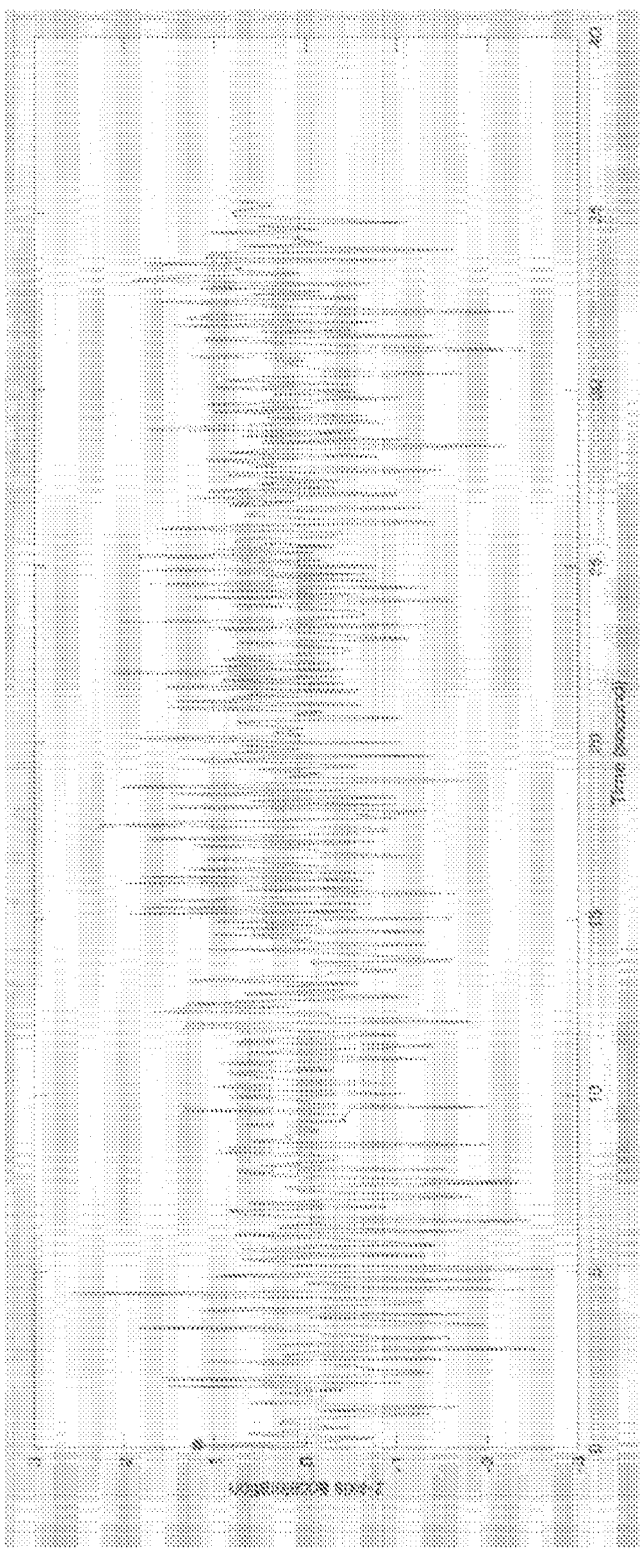
FIG. 15 is a screenshot of a video in which the z-axis acceleration data sampled at 1,600 Hz was converted to an audio file. Scratching activity creates rough and periodic sounds.
Figure 16:
FIG. 16 is a screenshot of a video in which the z-axis acceleration data sampled at 1,600 Hz was converted to an audio file. Compared with scratching sound, the sound of hand waving motion do not contain perceivable periodicity or sound.

Clearly, the classification results according to the invention are a significant improvement from most of the prior work on automated scratch detection. Table 2 is a summary of relevant studies that were strictly validated with video recorded data. FIG. 14 is a screenshot of a video illustrates a pediatric patient with AD wearing the ADAM sensor while scratching. The IR camera demonstrates scratching behavior that is subsequently coded. Note that scratching intensity varied from the beginning to the end of the scratching event, as reflected in the IR video as a rigorous scratching motion and in the ADAM sensor data as a large amplitude signal.

TABLE 2

Comparison with prior arts in automated scratch detection (N/R: not reported).

| Study | Moreau et al. [15] | Ikoma et al. [18] | Present Study |
|---|---|---|---|
| Year | 2017 | 2019 | 2021 |
| Sensitivity | 66.0% | 84.6% | 84.3% |
| Precision | 71.0% | N/R | 82.5% |
| F1 | 68.0% | N/R | 82.9% |
| Accuracy | N/R | N/R | 99.0% |
| Subjects (hours) | 26 (168 h) | 5 (N/R) | 21 (381 h) |
| Form Factor | Watch | Watch | Patch |
| Laboratory Validation | Yes | Yes | Yes |
| Free-Living Validation | Yes | No | Yes |
| Patient population | Yes | Yes | Yes |

While the objective classifier optimized in this study was the RF classifier, the performances of other classifiers such as logistic regression and gradient boosting, were computed for comparison and are listed in Table 3, using the training data. Logistic regression and gradient boosting classifiers showed poor sensitivity. While gradient boosting classifier had low sensitivity (67%), it exhibited the greatest specificity. We observed the best sensitivity, F1 and accuracy with the RF classifier, and the best specificity was observed with the gradient boosting classifier.

TABLE 3

Classification performance of different classifiers.

| | Sensitivity | Specificity | F1 | Accuracy |
|---|---|---|---|---|
| Logistic Regression | 61.8% | 84.1% | 68.0% | 69.1% |
| Random Forest | 87.8% | 88.1% | 89.8% | 89.1% |
| Gradient Boosting | 67.1% | 95.6% | 76.9% | 76.9% |

Inter-Rater Reliability

For the clinical validation study, infrared (IR) video served as the ground truth. Annotation was performed based on visual inspection and human judgement. To evaluate the inter-rater reliability of annotation, annotation was performed again by a different researcher (EA, HC) on data from three patients within the validation data set. The labels from two researchers were compared using Fleiss' kappa. The average of kappa was 0.88. According to Landis and Koch, annotations with such a kappa value are considered to be in good agreement.

Discussion

Itch is one of the most common clinical symptoms of disease affecting both children and adults across skin and non-skin conditions. Despite the prevalence of itch and its profound impact on quality of life, accurate and convenient methods to fully characterize itch and itch-associated scratching behavior do not exist, for use either in clinical practice or in the home. Technologies that are able to precisely and reliably assess itch will serve as critically important tools for drug development, quantification of itch severity and monitoring of treatment response.

Video surveillance with manual labeling is considered the gold standard as it allows accurate identification and quantification of scratching behavior. This technique is, however, both labor intensive and difficult to automate. These drawbacks, taken together with a range of associated privacy concerns, render this approach impractical for routine use. Wrist-bound accelerometers represent popular tools for collecting objective data in a wide range of clinical studies, with adequate sensitivity but poor specificity. Some studies cast doubt on the clinical applicability of actigraphy data, due partly to poor correlations with AD disease severity and quality of life. Emerging approaches that exploit smartwatches in combination with machine learning algorithms outperform simple actigraphy-based methods. However, these systems cannot detect finger-only scratching, and hand waving and related gestures are misclassified as scratching (FIGS. 3A-3B). As an example of an unusual approach, Noro et al. developed a wristwatch-shaped sound detection system to measure scratching sounds through bone conduction. Although the accuracy can approach that of video analysis, microphone-based systems involve significant privacy concerns, and their performance degrades with ambient noise.

Figure 11:
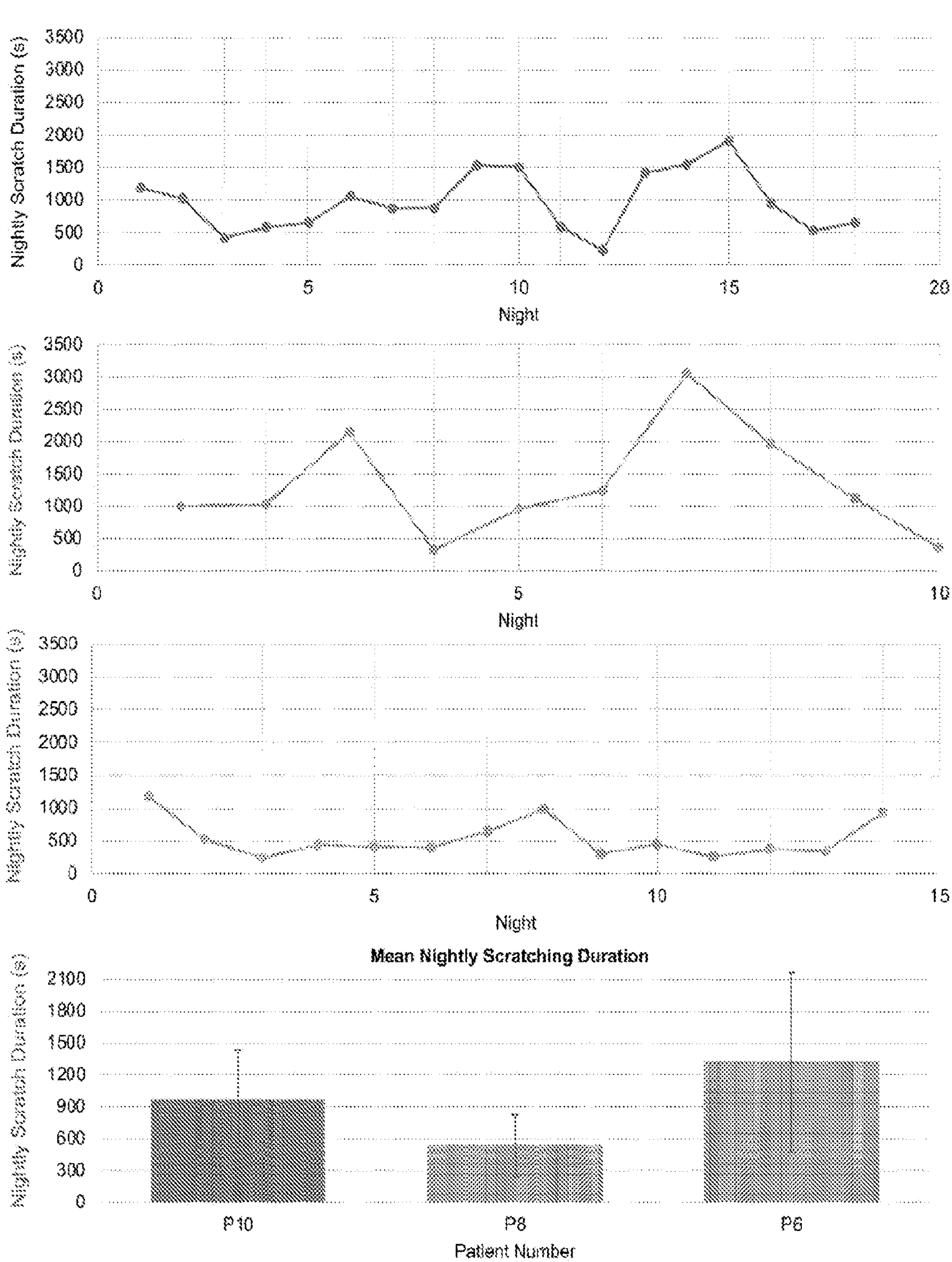
FIG. 11 shows a subset of 3 AD patients wore the sensors longer than 7 days to illustrate long term scratch behavior according to embodiments of the invention. These individuals also initiated a new topical medicine (crisaborole) to evaluate treatment benefit. Scratch durations of AD patients were obtained based on the scratch predictions of the scratch detection algorithm. The scratch durations of AD patients varied from patient to patient based on the severity of their symptoms, and significant variations were observed for a single patient across multiple nights.

The ADAM sensor and scratch algorithm reported here offer key advantages. First, the soft flexible nature of the devices allows them to conform to the hands of a wide range of patients, as validated on children as young as four to full-grown adults, where they remain softly but robustly adhered during a range of natural activities. Such aspect of the ADAM sensor is particularly suitable for investigating long-term changes of pathological symptoms such as nocturnal pruritus. For instance, with the ADAM sensor, we observed significant nightly variation in scratching in a subset of patients with AD who wore the sensor for an extended period of time (10 days or more). This implies that averaging scratch duration over a more sustained period of wear time is likely necessary rather than a single night (FIG. 11). Second, the system captures both low and high frequency acousto-mechanic signatures associated with scratching. The ability to effectively capture "acoustic" signals generated by scratching, without the need for a microphone, ensures both patient privacy and performance in noisy environments with no deterioration in signal quality. Finally, the system is waterproof, wireless, and rechargeable with 7 days of continuous operating efficiency. These features enhance the ease of use and reduce user burden in both clinical practice and research trials.

Several limitations must, however, be noted. First, the clinical validation studies reported here involve only n=11 subjects, due partly to the high degree of manual labor required to evaluated IR camera footage. However, this represents one of the largest cohorts studied to date for scratching (Table 2) given the time intensity of data labeling. Future efforts will include additional patient testing across a wide range of clinical conditions beyond AD, with patients even younger than those studied here. Nevertheless, the findings in this paper clearly show that training on healthy normal subjects performing voluntary scratching activities can apply successfully to clinical data in a predominately pediatric population affected by AD. The outcomes, which follow from the unique distinguishing features in the data from the ADAM device, suggest remarkable levels of generalizability, as well as opportunities to develop algorithms tailored to patient populations. Second, all measurements of scratching described here focus only on the dominant hand of the subjects. An additional sensor on the contralateral hand will provide additional information. Previous studies indicate no difference in scratching tendency for dominant or non-dominant hands, suggesting that a single sensor does not lead to significant information loss. Third, the clinical validation studies focus on AD patients only. Future work will examine applications to other medical conditions where itch is a predominant symptom. As a final comment, AD affects sleep to a significant degree, particularly in children. The ADAM sensor itself can recapitulate sleep stages against polysomnography, the gold standard method to assess sleep. An immediate opportunity for additional work is in using two, time-synchronized ADAM sensors to assess both scratch and sleep concomitantly.

CONCLUSION

This exemplary study reports a unique hand-mounted, soft, flexible sensor and a data analysis pipeline for detecting scratching activities using high-frequency 3-axis accelerometer data that capture features associated with both motions and acousto-mechanical signals. From a training study conducted with 10 participants, detection of scratching activity has an overall accuracy of 89.1% with a sensitivity of 87.8%, and specificity of 88.1%. Clinical validation studies with 11 participants reveal an overall accuracy of 99.0% with a sensitivity of 84.3% and specificity of 99.3%, even in naturalistic home environments. The small, flexible characteristics of the ADAM sensor and its reusability are key features that allow deployment in both research and clinical care settings. The promising results presented herein highlight suggest utility as a powerful methodological tool with the potential to accurately capture scratching activities not only in patients with atopic dermatitis but also in patients suffering from any generalized pruritic disorder.

This invention discloses, among other things, a non-invasive technology to objectively quantify scratching behavior via a soft, flexible, and wireless sensor that captures the acousto-mechanic signatures of scratching from the dorsum of the hand. A machine learning algorithm validated on data collected from healthy subjects (n=10) indicates excellent performance relative to smartwatch-based approaches. Clinical validation in a cohort of predominately pediatric patients (n=11) with moderate to severe atopic dermatitis included 46 sleep-nights totaling about 378.4 hours. The data indicate an accuracy of about 99.0% (about 84.3% sensitivity, about 99.3% specificity) against visual observation. This work suggests broad capabilities relevant to applications ranging from the assessing the efficacy of drugs for conditions that cause itch, to monitoring disease severity and treatment response.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

LIST OF REFERENCES

[1] G. Yosipovitch, M. W. Greaves and M. Schmelz, Itch. *Lancet.* 361, 690-694 (2003).

[2] A. Bathe, E. Weisshaar, U. Matterne, Chronic pruritus-more than a symptom: a qualitative investigation into patients' subjective illness perceptions. *J. Adv. Nurs.* 69, 316-326 (2013).

[3] M. Shive, E. Linos, T. Berger, M. Wehner, M.-M. Chren, Itch as a patient-reported symptom in ambulatory care visits in the United States. *J. Am. Acad. Dermatol.* 69, 550-556 (2013).

[4] T. E. Shaw, G. P. Currie, C. W. Koudelka, E. L. Simpson, Eczema prevalence in the United States: data from the 2003 National Survey of Children's Health. *J. Invest. Dermatol.* 131, 67-73 (2011).

[5] S. L. Chamlin, C. L. Mattson, I. J. Frieden, M. L. Williams, A. J. Mancini, D. Cella, M.-M. Chren, The price of pruritus: sleep disturbance and cosleeping in atopic dermatitis. *Arch. Pediatr. Adolesc. Med.* 159, 745-750 (2005).

[6] K. Hon, T. Leung, K. Wong, C. Chow, A. Chuh, P. Ng, Does age or gender influence quality of life in children with atopic dermatitis? *Clin. Exp. Dermatol.* 33, 705-709 (2008).

[7] D. Camfferman, J. D. Kennedy, M. Gold, A. J. Martin, K. Lushington, Eczema and sleep and its relationship to daytime functioning in children. *Sleep Med Rev.* 14, 359-369 (2010).

[8] R. Sack, J. Hanifin, Scratching below the surface of sleep and itch. *Sleep Med Rev.* 14, 349-350 (2010).

[9] A. B. Fishbein, O. Vitaterna, I. M. Haugh, A. A. Bavishi, P. C. Zee, F. W. Turek, S. H. Sheldon, J. I. Silverberg, A. S. Paller, Nocturnal eczema: review of sleep and circadian rhythms in children with atopic dermatitis and future research directions. *J. Allergy Clin. Immunol.* 136, 1170-1177 (2015).

[10] A. B. Fishbein, K. Mueller, L. Kruse, P. Boor, S. Sheldon, P. Zee, A. S. Paller, Sleep disturbance in children with moderate/severe atopic dermatitis: a case-control study. *J. Am. Acad Dermatol.* 78, 336-341 (2018).

[11] J. I. Silverberg, N. K. Garg, A. S. Paller, A. B. Fishbein, P. C. Zee, Sleep disturbances in adults with eczema are associated with impaired overall health: a US population-based study. *J. Invest. Dermatol.* 135, 56-66 (2015).

[12] M. K. LeBourgeois, D. C. Dean, S. C. Deoni, M. Kohler, S. Kurth, A simple sleep EEG marker in childhood predicts brain myelin 3.5 years later. *NeuroImage.* 199, 342-350 (2019).

[13] G. Kiebert, S. V. Sorensen, D. Revicki, S. C. Fagan, J. J. Doyle, J. Cohen, D. Fivenson, "Atopic dermatitis is associated with a decrement in health-related quality of life. *Int. J. Dermatol.* 41, 151-158 (2002).

[14] C. S. Murray, J. L. Rees, Are subjective accounts of itch to be relied on? The lack of relation between visual analogue itch scores and actigraphic measures of scratch. *Acta Derm. Vener.* 91, 18-23 (2011).

[15] A. Moreau, P. Anderer, M. Ross, A. Cerny, T. H. Almazan, B. Peterson, Detection of nocturnal scratching movements in patients with atopic dermatitis using accelerometers and recurrent neural networks. *IEEE J. Biomed. Health Inform.* 22, 1011-1018 (2017).

[16] K. Lee, X. Ni, J. Y. Lee, H. Arafa, J. P. David, S. Xu, R. Avila, M. Irie, J. H. Lee, R. L. Easterlin, Mechano-acoustic sensing of physiological processes and body motions via a soft wireless device placed at the suprasternal notch. *Nat. Biomed Eng.* 4, 148-158 (2020).

[17] Y. Shao, V. Hayward, Y. Visell, Spatial patterns of cutaneous vibration during whole-hand haptic interactions. *PNAS,* 113, 4188-4193 (2016).

[18] A. Ikoma, T. Ebata, L. Chantalat, K. Takemura, F. Mizzi, M. Poncet, D. Leclercq, Measurement of nocturnal scratching in patients with pruritus using a smartwatch: initial clinical studies with the itch tracker app. *Acta Derm. Vener.* 99, 268-273 (2019).

[19] J. Lee, D. Cho, J. Kim, E. Im, J. Bak, K. H. Lee, K. H. Lee, J. Kim, Itchtector: a wearable-based mobile system for managing itching conditions. *Proc. CHI Conf. Hum. Factor. Comput. Syst.* 893-905 (2017).

[20] K. Benjamin, K. Waterston, M. Russell, O. Schofield, B. Diffey, J. L. Rees, The development of an objective method for measuring scratch in children with atopic dermatitis suitable for clinical use. *J. Am. Acad. Dermatol.* 50, 33-40 (2004).

[21] M. Wiertlewski, J. Lozada, V. Hayward, The spatial spectrum of tangential skin displacement can encode tactual texture. *IEEE Trans. Robot.* 27, 461-472 (2011).

[22] M. Wiertlewski, V. Hayward, Mechanical behavior of the fingertip in the range of frequencies and displacements relevant to touch. *J. Biomech.* 45, 1869-1874 (2012).

[23] B. Delhaye, V. Hayward, P. Lefèvre, J.-L. Thonnard, Texture-induced vibrations in the forearm during tactile exploration. *Front. Behav. Neurosci.* 6, 37 (2012).

[24] S. Saeb, L. Lonini, A. Jayaraman, D. C. Mohr, K. P. Kording, The need to approximate the use-case in clinical machine learning. *Gigascience.* 6, gix019 (2017).

[25] T. Ebata, H. Aizawa, R. Kamide, An infrared video camera system to observe nocturnal scratching in atopic dermatitis patients. *J. Dermatol.* 23, 153-155 (1996).

[26] T. Ebata, S. Iwasaki, R. Kamide, M. Niimura, Use of a wrist activity monitor for the measurement of nocturnal scratching in patients with atopic dermatitis. *Br. J. Dermatol.* 144, 305-309 (2001).

[27] Y. Noro, Y. Omoto, K. Umeda, F. Tanaka, Y. Shiratsuka, T. Yamada, K. Isoda, K. Matsubara, K. Yamanaka, E. C. Gabazza, Novel acoustic evaluation system for scratching behavior in itching dermatitis: rapid and accurate analysis for nocturnal scratching of atopic dermatitis patients. *J. Dermatol.* 41, 233-238 (2014).

[28] O. Crasborn, H. Sloetjes, E. Auer, P. Wittenburg, Combining video and numeric data in the analysis of sign languages with the ELAN annotation software. *2nd workshop on the representation and processing of sign languages: lexicographic matters and didactic scenarios.* 82-87 (2006).

[29] S. Arlot, A. Celisse, A survey of cross-validation procedures for model selection. *Statistics surveys.* 4, 40-79 (2010).

[30] R. Kohavi, A study of cross-validation and bootstrap for accuracy estimation and model selection. *IJCAI.* 14, 1137-1145 (1995).

[31] J. L. Fleiss, J. Cohen, B. S. Everitt, Large sample standard errors of kappa and weighted kappa. *Psychol. Bull.* 72, 323 (1969).

[32] J. R. Landis and G. G. Koch, The measurement of observer agreement for categorical data. *Biometrics.* 159-174 (1977).

What is claimed is:

1. An acousto-mechanic sensor, comprising:

at least one inertial measurement unit (IMU) for operably detecting vibratory and motion signatures of physiological processes comprising scratching or rubbing activities; and a plurality of electronic components comprising a microcontroller unit (MCU) coupled to the at least one IMU for receiving data from the at least one IMU and processing the received data, and a wireless communication system for wireless data transmission, wherein the acousto-mechanic sensor is configured to measure signals of both low frequency less than about 100 Hz and high frequency greater than about 100 Hz derived from the at least one IMU;

wherein the acousto-mechanic sensor is skin mounted to allow for coupling of the at least one IMU to the skin for capture of both the high frequency and low frequency signals; and wherein the high frequency and low frequency signals are representative of a physiological response to itch as a scratching or rubbing activity; and wherein the acousto-mechanic sensor is capable of capturing both motion and bone-conducted high frequency vibrations that are specific for scratching, so as to differentiate the motion of scratching from true scratching on the skin.

2. The acousto-mechanic sensor of claim 1, wherein the plurality of electronic components and the at least one IMU are separated so that the plurality of electronic components is in one end of the acousto-mechanic sensor and the at least one IMU is in the other end of the acousto-mechanic sensor.

3. The acousto-mechanic sensor of claim 1, further comprising a flexible printed circuit board (fPCB) for supporting and interconnecting the at least one IMU and the plurality of electronic components.

4. The acousto-mechanic sensor of claim 3, wherein the fPCB has a patterned layout that includes a plurality of freely deformable, serpentine interconnects, designed to mechanically decouple the at least one IMU from the other components of the acousto-mechanic sensor, wherein the plurality of freely deformable, serpentine interconnects is flexible and stretchable and adapted for interconnecting the at least one IMU and the plurality of electronic components.

5. The acousto-mechanic sensor of claim 3, further comprising an elastomeric encapsulation layer at least partially surrounding the at least one IMU, the plurality of electronic components and the fPCB to form a tissue-facing surface operably attached to the living subject, wherein the tissue-facing surface of the elastomeric encapsulation layer is configured to conform to a skin surface of the living subject.

6. The acousto-mechanic sensor of claim 5, wherein the encapsulation layer is formed of a thin, low modulus silicone elastomer, wherein the elastomeric encapsulation layer is a biocompatible silicone enclosure.

7. The acousto-mechanic sensor of claim 1, further comprising a biocompatible hydrogel adhesive for attaching the acousto-mechanic sensor on an anatomical location of a living subject.

8. The acousto-mechanic sensor of claim 7, wherein the biocompatible hydrogel adhesive is a medical-grade, hypoallergenic adhesive.

9. The acousto-mechanic sensor of claim 7, wherein the biocompatible hydrogel adhesive is adapted such that signals from the living subject are operably conductible to the at least one IMU.

10. The acousto-mechanic sensor of claim 1, wherein the wireless communication system comprises a Bluetooth low energy (BLE) radio.

11. The acousto-mechanic sensor of claim 1, wherein the wireless communication system is configured to send an output signal from the acousto-mechanic sensor to an external device.

12. The acousto-mechanic sensor of claim 1, wherein in the plurality of electronic components further comprises a power module coupled to the at least one IMU, the wireless communication system and the MCU for providing power thereto.

13. The acousto-mechanic sensor of claim 12, wherein the power module comprises a battery, wherein the battery is a rechargeable battery.

14. The acousto-mechanic sensor of claim 13, wherein the power module further comprises a wireless charging module for wirelessly charging the rechargeable battery;

and a failure prevention element including a short-circuit protection component or a circuit to avoid battery malfunction.

15. The acousto-mechanic sensor of claim 1, wherein the at least one IMU comprises a millimeter-scale, three-axis accelerometer configured to detect tissue-conducted vibrations and motions associated with scratching activities.

16. The acousto-mechanic sensor of claim 15, wherein the three-axis accelerometer is configured to detect acceleration along the x-axis and y-axis at a first sample rate, and acceleration along the z-axis at a second sample rate, wherein the x-axis and y-axis are oriented parallel to a skin surface on which the acousto-mechanic sensor is attached, and the z-axis is perpendicular to the skin surface, wherein the first sample rate is in a range of about 160-240 Hz, and the second sample rate is in a range of about 1,200-2,000 Hz.

17. The acousto-mechanic sensor of claim 15, wherein the three-axis accelerometer is configured to have a sampling rate of about 1,600 Hz at a resolution of 16 bits and a dynamic range of about ±2g, wherein g is the gravitational acceleration, 9.8 $m/s^2$.

18. The acousto-mechanic sensor of claim 15, wherein when placed on the dorsum of the hand, the acousto-mechanic sensor is able to detect acousto-mechanic signals associated with the scratching activities via a combination of motion and acousto-mechanic signals, in a manner that is immune to ambient noise.

19. The acousto-mechanic sensor of claim 15, wherein when placed between the second and third finger metacarpal bones, the acousto-mechanic sensor is able to quantify the scratching activities initiated not only from motions of the wrist and/or arm, but from the fingers and fingertips as well, across a wide temporal bandwidth that includes high frequency vibratory motions associated with scratching itself.

20. The acousto-mechanic sensor of claim 15, wherein the scratching activities are characterized with first and second types of signals, wherein the first type of signals corresponds to gross movements of the hand, and the second type of signals, overlapping in time with the first type of signals, arises from subtle vibratory impulses generated by motions of the fingertips and fingernails against a contacting surface.

21. The acousto-mechanic sensor of claim 20, wherein the first type of signals has characteristic frequencies in the range of a few Hz or less, and the second type of signals has characteristic frequencies extending into the range of a few hundred Hz and amplitudes decaying rapidly with position along the fingers and into the hand, and eventually passing through the wrist and to the arm.

22. The acousto-mechanic sensor of claim 20, wherein the first and second types of signals are identified by passing the data through low pass and high pass filters with cutoffs at about 2 Hz.

23. The acousto-mechanic sensor of claim 15, wherein signal features that uniquely characterize the scratching activities are extracted from the output signals of the acousto-mechanic sensor to train and validate a machine learning-based algorithm for scratch detection so as to quantify symptoms of pruritus.

24. The acousto-mechanic sensor of claim 1, being configured to perform scratch algorithms on the data detected from the at least one IMU so as to obtain signal features that uniquely characterize the scratching activities.

25. The acousto-mechanic sensor of claim 1, being configured to notify the user and/or professionals, via haptic/audio/visual means of the acousto-mechanic sensor, mobile devices, and/or smart wearable devices.

26. The acousto-mechanic sensor of claim 1, being flexible and conformable to the skin with a specific geometrical polarity for mounting in an anatomical location of the living subject.

27. The acousto-mechanic sensor of claim 1, being operably placed over key bones including the metatarsals of the first and second digits to capture high frequency vibrations that are specific to scratching.

28. The acousto-mechanic sensor of claim 1, having the low profile conformable nature that allows placement of the acousto-mechanic sensor on the curvilinear surface of the dorsal hand for capturing scratching no matter the articulation of the joint, wherein said scratching is associated with finger movements only, wrist movements only, elbow movements only, shoulder movements only, or a combination of them.

29. The acousto-mechanic sensor of claim 1, being operably placed on the dorsum of the hand, finger nail, finger, or wrist, for measuring scratching motions of any time.

30. The acousto-mechanic sensor of claim 1, being usable in any condition where itch is a symptom as a diagnosis, treatment response indicator, clinical trials endpoint, or early warning of worsening disease.

31. A method for quantifying symptoms of pruritus, comprising:

- attaching an acousto-mechanic sensor of claim 1 to an anatomical location of a living subject;
- detecting, by the acousto-mechanic sensor, signals associated with scratching and/or non-scratching activities; and
- analyzing the signals to evaluate acousto-mechanic signatures of scratching so as to quantify symptoms of pruritus,
- wherein said analyzing the signals comprises:
  - preprocessing the signals to remove low frequency baseline wandering caused by slow, large-scale motions, so that the preprocessed signals contain more specific high frequency signal components associated with z-axis acceleration;
  - segmenting the preprocessed signals into frames by sliding a n-second window with an overlap;
  - extracting a set of features from each frame; and
  - applying a random forest (RF) classifier to the set of extracted features for prediction and validation; and
  - wherein the RF classifier is trained with a training data set contains scratching data from a plurality of body locations and various types of non-scratching activities collected from a number of healthy living subjects.

32. The method of claim 31, wherein said analyzing the signals further comprises:

- assigning each frame a label of 0 that indicates non-scratching activity, if less than about 50% of data points in a given frame are labeled as scratching activity, otherwise, assigning the frame a label of 1 that indicates scratching activity.

33. The method of claim 31, wherein the n-second window is a 1-second window.

34. The method of claim 31, wherein the overlap is in a range of about 50%-90% overlap.

35. The method of claim 31, wherein the RF classifier is optimized by comparing results from leave-one-subject-out cross validation (LOSO-CV) applied to the training data set, wherein the results form the basis for optimization of the RF classifier.

36. The method of claim 35, wherein parameters for the optimization comprises a number of decision trees in the RF classifier and a minimum required scratching (MRS) duration, wherein the number of decision trees is in a range from about 10 to about 200.

37. The method of claim 36, wherein for the optimization, the RF classifier returns predictions at a 1-second frame level, and the outputs are subsequently clustered using density-based spatial clustering of applications with noise (DBSCAN), so as to join two scratching frames in close proximity as a single scratching event, wherein the MRS duration defines the minimum number of frames to form a cluster of scratching events, wherein the MRS duration is in a range from about 1.5 to 8.5 seconds.

38. The method of claim 31, wherein the scratching and/or non-scratching activities comprises scratching at the head, the arm, the abdomen, the knee and/or the leg of the living subject, and/or simulating scratching in the air, hand waving, texting on the phone, typing a keyboard, and/or clicking a mouse.

39. The method of claim 31, wherein the anatomical location is at the fingertip, finger, dorsum of the hand, and the wrist of the living subject.

40. The method of claim 31, wherein the set of features comprises variability of acceleration in x/y/z axis, high frequency spectrogram, and/or low frequency spectrogram.

41. A non-transitory tangible computer-readable medium storing instructions which, when executed by one or more processors, cause the method of claim 31 to be performed.

* * * * *